US009668846B2

(12) United States Patent
Lelkes et al.

(10) Patent No.: US 9,668,846 B2
(45) Date of Patent: Jun. 6, 2017

(54) TEXTILE-TEMPLATED ELECTROSPUN ANISOTROPIC SCAFFOLDS FOR TISSUE ENGINEERING AND REGENERATIVE MEDICINE

(75) Inventors: Peter I. Lelkes, Cherry Hill, NJ (US); H. Gozde Senel, Philadelphia, PA (US); David Brookstein, Fort Washington, PA (US); Muthu Govindaraj, Harleysville, PA (US)

(73) Assignees: Drexel University, Philadelphia, PA (US); Philadelphia University, Philadelphia, PA (US)

( * ) Notice: Subject to any disclaimer, the term of this patent is extended or adjusted under 35 U.S.C. 154(b) by 1203 days.

(21) Appl. No.: 13/699,442

(22) PCT Filed: May 23, 2011

(86) PCT No.: PCT/US2011/037557
§ 371 (c)(1),
(2), (4) Date: Feb. 6, 2013

(87) PCT Pub. No.: WO2011/149836
PCT Pub. Date: Dec. 1, 2011

(65) Prior Publication Data
US 2013/0131830 A1 May 23, 2013

Related U.S. Application Data

(60) Provisional application No. 61/347,722, filed on May 24, 2010.

(51) Int. Cl.
| A61F 2/00 | (2006.01) |
| C12M 1/12 | (2006.01) |
| C12N 11/08 | (2006.01) |
| A61L 27/26 | (2006.01) |
| A61L 27/38 | (2006.01) |

(52) U.S. Cl.
CPC ............ *A61F 2/0063* (2013.01); *A61L 27/26* (2013.01); *A61L 27/3826* (2013.01); *C12M 25/14* (2013.01); *C12N 11/08* (2013.01)

(58) Field of Classification Search
CPC ..... A61L 27/26; A61L 27/3826; C12N 11/08; C12M 25/14; A61F 2/0063; C08L 67/04; C08L 89/00
See application file for complete search history.

(56) References Cited

U.S. PATENT DOCUMENTS

| 2003/0100944 A1 | 5/2003 | Laksin et al. |
| 2005/0073075 A1 | 4/2005 | Chu et al. |
| 2006/0204539 A1 | 9/2006 | Atala et al. |
| 2007/0276507 A1 | 11/2007 | Bertram et al. |
| 2008/0009830 A1 | 1/2008 | Fujimoto et al. |
| 2008/0109070 A1 | 5/2008 | Wagner et al. |
| 2009/0142836 A1 | 6/2009 | Wang et al. |
| 2010/0327494 A1 | 12/2010 | Jabbari |

FOREIGN PATENT DOCUMENTS

| WO | 2009/069759 | 6/2009 |
| WO | 2009/127166 | 10/2009 |

OTHER PUBLICATIONS

Neves et al, Patterning of polymer nanofiber meshes by electrospinning for biomedical applications, International Journal of Nanomedicine, 2007, 2, pp. 433-448.*
Li et al, Co-electrospun poly(lactide-co-glycolide), gelatin, and elastin blends for tissue engineering scaffolds, J Biomed Mater Res, 2006, 79A, pp. 963-973.*
Caracciolo et al, Electrospinning of novel biodegradable poly(ester urethane)s and poly(ester urethane urea)s for soft tissue-engineering applications, J Mater Sci: Mater Med, 2009, 20, pp. 2129-2137.*
Srivastava et al, Microfluidic electrospinning of biphasic nanofibers with Janus morphology, Biomicrofluidics, 2009, 3, pp. 012801-1 to 012801-6.*
Senel-Ayaz, et al., "Textile-Templated Electrospun Anisotropic Scaffolds for Tissue Engineering and Regenerative Medicine," *2010 Annual International Conferences of the IEEE, Engineering in Medicine and Biology Society* [online], Aug. 31, 2010-Sep. 4, 2010, pp. 255-258, retrieved from the internet <URL:http://www.philau.edu/today/pdf/IEEE-paper-090110.pdf>.
Geary, et al., "Characterisation of Bionate polycarbonate polyurethanes for orthopaedic applications," *J Mater Sci: Mater Med*, 2008, 19:3355-3363.

* cited by examiner

Primary Examiner — Julie Ha
Assistant Examiner — Li Ni Komatsu
(74) Attorney, Agent, or Firm — Saul Ewing LLP; Kathryn Doyle; Brian R. Landry

(57) ABSTRACT

The present invention includes an anisotropic scaffold, which is prepared by electrospinning a solution of matrix material upon a textile template. The present invention further includes a method of preparing such scaffold. The anisotropic scaffold of the invention finds use in tissue engineering and regenerative medicine.

25 Claims, 16 Drawing Sheets

Acc V 10.00kV
Spot 3.0
Magn 100x
Det SE
WD 9.8
5% PLGA-CT

Acc V 10.00kV
Spot 3.0
Magn 100x
Det SE
WD 10.1
5% PLGA-TG

Drexel MCF
Zeiss Supra 50 VP
EHT = 5.00 kV
Magn = 100x
WD = 12 mm
Vacuum Mode = High Vacuum
Detector = SE2

Drexel MCF
Zeiss Supra 50 VP
EHT = 5.00 kV
Mag = 100x
WD = 12 mm
Vacuum Mode = High Vacuum
Detector = SE2

Drexel MCF
Zeiss Supra 50 VP
EHT = 5.00 kV
Mag = 100x
WD = 11 mm
Vacuum Mode = High Vacuum
Detector = SE2

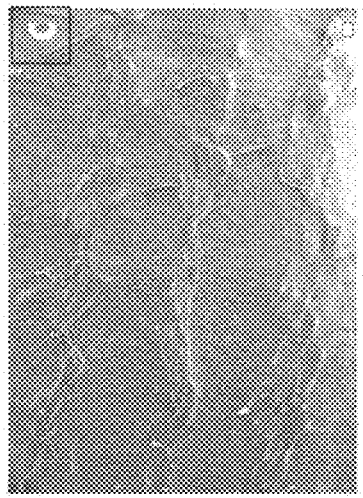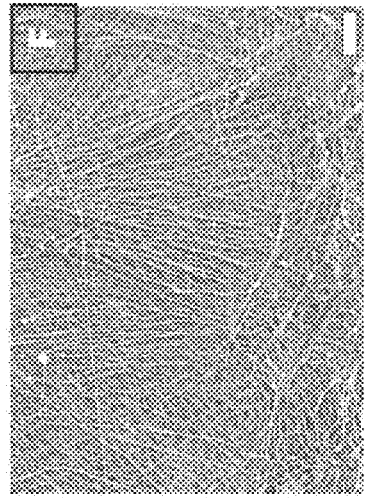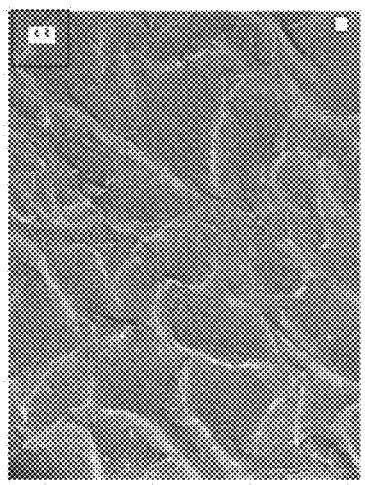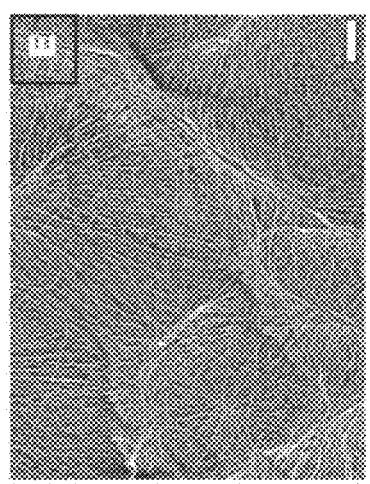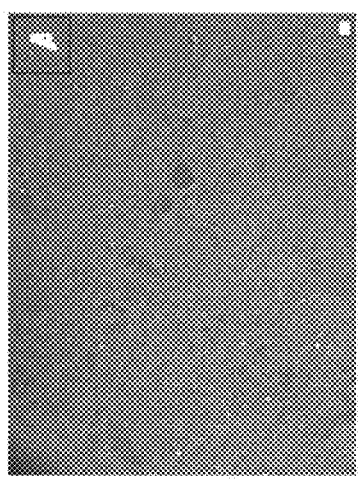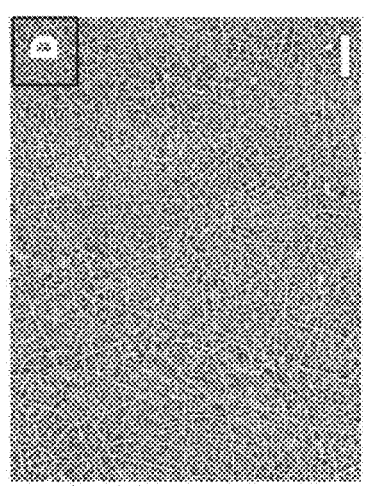
Fig. 5

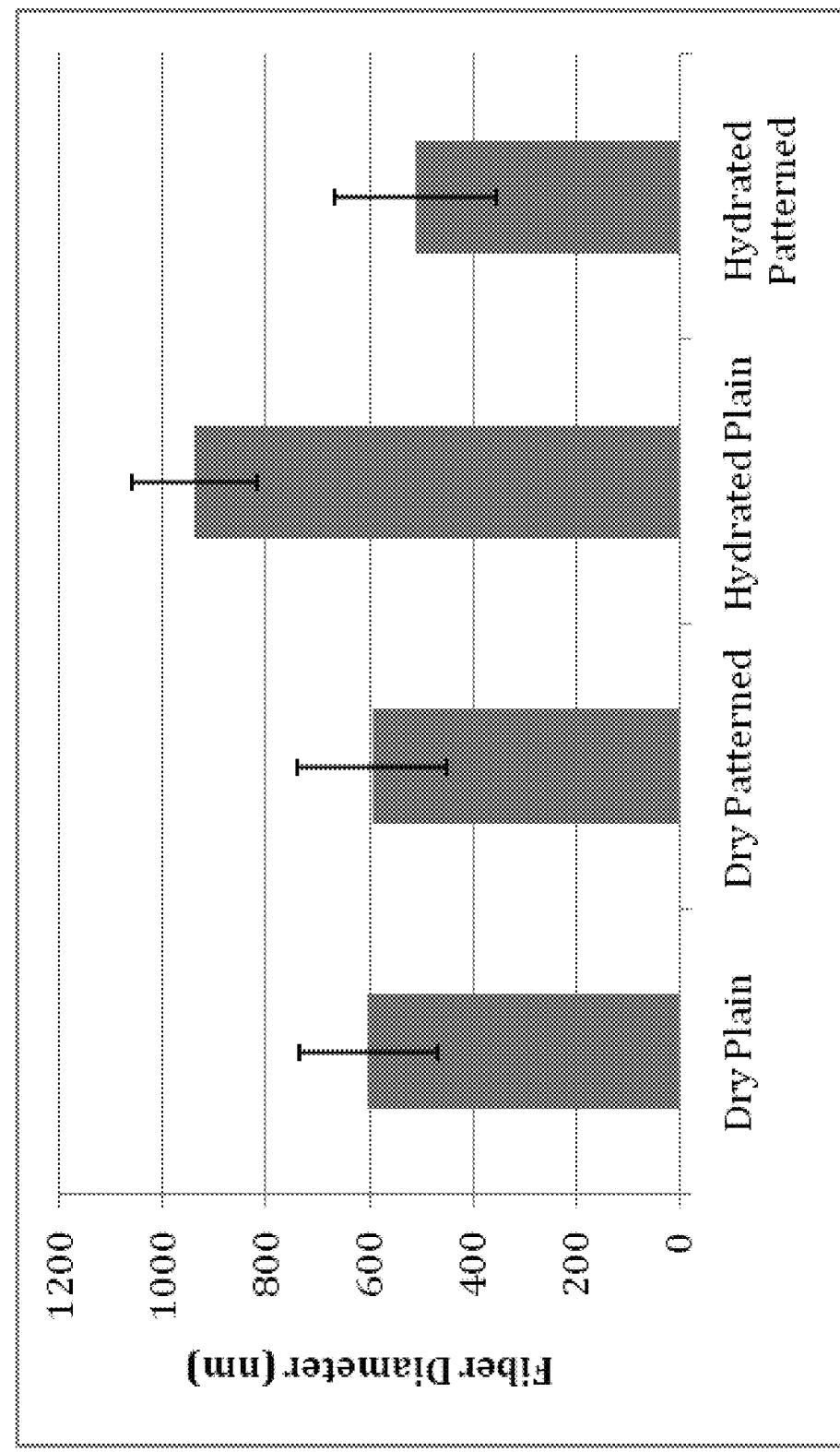

TEXTILE-TEMPLATED ELECTROSPUN ANISOTROPIC SCAFFOLDS FOR TISSUE ENGINEERING AND REGENERATIVE MEDICINE

CROSS-REFERENCE TO RELATED APPLICATIONS

The present application is a 35 U.S.C. §371 national phase application from, and claiming priority to, International Application No. PCT/US11/37557, filed May 23, 2011, and published under PCT Article 21(2) in English, which claims the benefit of U.S. Provisional Application No. 61/347,722, filed May 24, 2010, all of which applications are hereby incorporated by reference in their entireties herein.

STATEMENT REGARDING FEDERALLY SPONSORED RESEARCH OR DEVELOPMENT

This invention was made with government support under Contract No. W911QY-10-1-0002 awarded by the U.S Army Natick Soldier Systems Center via a subcontract from Philadelphia University for the Department of Defense's Pennsylvania Advanced Textile Research and Innovation Center (PATRIC). The government has certain rights in the invention.

BACKGROUND OF THE INVENTION

Tissue engineering is an area of biomaterials research that combines cellular biology, engineering science and materials science to develop artificial tissues that may be used to repair or replace body tissues, such as bone, cartilage, blood vessels, bladder and skin. Recent developments in the field of tissue engineering have yielded novel tissue replacement strategies. Scientific advances in biomaterials, stem cells, growth and differentiation factors, and biomimetic environments have allowed the preparation of artificial tissues by combining engineered extracellular matrices, cells, and biologically active molecules. Among the major challenges now facing scientists is the development of laboratory-grown, structurally complex artificial tissues that are functionally and biomechanically stable and acceptable for transplantation procedures, since the artificial tissue must have specific mechanical and structural properties to function properly within the body.

In tissue engineering, cells are often implanted or "seeded" into an artificial structure capable of supporting three-dimensional tissue formation. These structures, typically called "scaffolds," often play an important role, both ex vivo and in vivo, of reproducing the environment of cells in the body. Scaffolds usually serve at least one of the following purposes: allowing cell attachment and migration; delivering and retaining cells and biochemical factors; enabling diffusion of vital cell nutrients and expressed products; and/or exerting mechanical and biological influences to modify the behavior of the cellular phase.

Development of novel scaffolds for tissue engineering is an ongoing effort. The scaffold must be biocompatible, bioresorbable and mimic at least some of the structural and functional properties of the extracellular matrix. Additionally, much like their correlated tissue type, the scaffold must facilitate cell adhesion, allow tissue orientation and facilitate tissue functionality (Hutmacher et al., 2001, J. Biomed. Mat. Res. 55(2):203-16). Therefore, it is important to generate a three-dimensional scaffold that provides the mechanical properties of the native tissue (including its specific surface pattering), allowing cellular attachment, alignment and proliferation. As an example, myocardium is made up of thick collagen matrix with well-aligned myocytes that lead to mechanical anisotropy (Jawad et al., 2008, Br. Med. Bull. 87:31-47). To be useful in myocardial tissue engineering, an artificial scaffold must have properties that enable it to mimic or support the native myocardium.

In order to achieve the goal of tissue reconstruction, the scaffold of choice must meet specific requirements. The scaffold must have an adequate level of porosity to facilitate cell seeding and diffusion of both cells and nutrients throughout the whole structure. Biodegradability is often an essential characteristic of the scaffold since it should preferably be absorbed by the surrounding tissues without the necessity of surgical removal. The rate at which scaffold degradation occurs has to coincide as much as possible with the rate of tissue formation. While cells are fabricating their own natural matrix structure around themselves, the scaffold provides structural integrity within the body. The scaffold will eventually break down within the body, leaving behind the newly formed tissue, which will take over the mechanical load.

Various materials (natural and synthetic, biodegradable and permanent) have been investigated as scaffolds. Most of these materials were already employed as bioresorbable sutures. Examples of these materials are collagen and polyesters. New biomaterials have been engineered to have ideal properties and functional customization, such as injectability, manufacturing ease, biocompatibility, non-immunogenicity, transparency, appropriate density, and appropriate resorption rates. A commonly used synthetic material is PLA (polylactic acid), a polyester that degrades within the human body to form lactic acid, which is naturally removed from the body. Other materials are polyglycolic acid (PGA) and polycaprolactone (PCL). Their degradation mechanisms are similar to that of PLA, but they exhibit respectively a faster and a slower rate of degradation compared to PLA. Scaffolds may also be constructed from natural materials. In particular, various derivatives of the extracellular matrix (collagen, fibrin, polysaccharides such as chitosan, or glycosaminoglycans such as hyaluronic acid) have been studied to evaluate their ability to support cell growth.

There remains a need to identify novel scaffolds that may be used in tissue engineering. Such scaffolds should be easily prepared and have three-dimensional anisotropic nanofibrous structures, which mimic the intrinsically anisotropic network and three-dimensionality of the tissue that needs to be repaired or replaced. The present invention fulfills this need.

BRIEF DESCRIPTION OF THE INVENTION

The invention includes a composition comprising an anisotropic scaffold, wherein the scaffold is prepared by electrospinning a solution of matrix material in a solvent upon a textile template.

In one embodiment, the matrix material comprises a protein. In another embodiment, the matrix material comprises a polymer. In yet another embodiment, the polymer is selected from the group consisting of poly(urethane), poly(siloxane), poly(ethylene), poly(vinyl pyrrolidone), poly(-hydroxy ethyl methacrylate), poly(N-vinyl pyrrolidone), poly(methyl methacrylate), poly(vinyl alcohol), poly(acrylic acid), polyacrylamide, poly(ethylene-co-vinyl acetate), poly (ethylene glycol), poly(methacrylic acid), polylactide, polyglycolide, poly(lactide-co-glycolide), polyanhydride, polyorthoester, polycarbonate, and combinations and copolymers thereof. In yet another embodiment, the polymer is poly(lactide-co-glycolide). In yet another embodiment, the polymer is polycarbonate urethane.

In one embodiment, the polymer is co-span with at least one compound selected from the group consisting of gelatin, elastin and mixtures thereof. In another embodiment, the polymer is poly(lactide-co-glycolide) and the polymer is co-span with gelatin and elastin. In yet another embodiment, the polymer is co-span with at least one conductive polymer. In yet another embodiment, the conductive polymer is selected from the group consisting of polyfluorene, polyphenylene, polypyrene, polyazulene, polynaphthalene, polypyrrole, polycarbazole, polyindole, polyazepine, polyaniline, polythiophene, poly(3,4-ethylenedioxythiophene), poly (p-phenylene sulfide), polyacetylene, poly(p-phenylene vinylene), and combinations and co-polymers thereof. In yet another embodiment, the conductive polymer is selected from the group consisting of polyaniline, polypyrrole and poly(3,4-ethylene-dioxythiophene). In yet another embodiment, the polymer is polycarbonate urethane. In yet another embodiment, the matrix material is biocompatible and cytocompatible.

In one embodiment, the solvent is selected from the group consisting of water, urea, methylene chloride, cyclohexane, diethyl ether, 1,4-dioxane, furan, tetrahydrofuran, ethanol, isopropanol, propane-1,3-diol, ethylene glycol, diethylene glycol, glycerine, acetone, 2-butanone, ethyl acetate, methyl formate, acetonitrile, acetamide, dimethylacetamide, N-methylformamide, N,N-dimethylformamide, N-methyl pyrrolidone, N-methyl morpholine-N-oxide, dimethylsulfoxide, formic acid, acetic acid, hydrochloric acid, maleic acid, 1,1,1-trifluoroacetone, hexafluoroacetone, 2,2,2-trifluoroethanol, 1,1,1,3,3,3-hexafluoro-2-propanol, monochloroacetic acid, trifluoroacetic acid, trifluoroacetic anhydride, triethanolamine, indole, piperazine, pyrrole, 2-pyrrolidone, pyridine, quinoline, tetrahydroquinoline, pyrazole, imidazole, and combinations thereof. In another embodiment, the solvent is 1,1,1,3,3,3-hexafluoro-2-propanol.

In one embodiment, the textile template is a knitted fabric. In another embodiment, the textile template is a woven fabric. In yet another embodiment, the textile template is polyester or cotton. In yet another embodiment, the yarn number of the textile varies from about 15 tex to about 75 tex. In yet another embodiment, the yarn number of the textile varies from about 20 tex to about 60 tex. In yet another embodiment, the weight of the textile varies from about 100 g/m² to about 300 g/m². In yet another embodiment, the thickness of the textile varies from about 0.8 mm to about 1.2 mm. In yet another embodiment, the thickness of the textile varies from about 0.9 mm to about 1.1 mm. In yet another embodiment, the fabric structure of the textile is Jersey (plain weft) knitted fabric. In yet another embodiment, the fabric construction of the textile varies from about 6 wale/cm to about 10 wale/cm. In yet another embodiment, the fabric construction of the textile varies from about 6 course/cm to about 8 course/cm.

In one embodiment, the textile template is peeled off from the scaffold. In another embodiment, cells are further immobilized on the scaffold. In yet another embodiment, the cells are myocytes.

The invention further includes a method of preparing an anisotropic scaffold. The method comprises the step of electrospinning a solution of matrix material in a solvent upon a textile template to form the anisotropic scaffold.

In one embodiment, the method further includes the step of peeling off the textile template from the anisotropic scaffold.

The invention also includes a method of preparing a cellularized anisotropic scaffold. The method includes the step of electrospinning a solution of matrix material in a solvent upon a textile template to form an anisotropic scaffold. The method further includes the optional step of coating the anisotropic scaffold with collagen. The method further includes the step of immobilizing cells on the anisotropic scaffold to form the cellularized anisotropic scaffold.

In one embodiment, the cells are myocytes.

The invention further includes a method of implanting a cellularized anisotropic scaffold in a subject in need thereof. The method comprises the step of electrospinning a solution of matrix material in a solvent upon a textile template to form an anisotropic scaffold. The method further comprises the optional step of coating the anisotropic scaffold with collagen. The method further comprises the step of immobilizing cells on the anisotropic scaffold to form the cellularized anisotropic scaffold. The method further comprises the step of implanting the cellularized anisotropic scaffold in the subject.

In one embodiment, the method further comprises the step of peeling off the textile template from the anisotropic scaffold before immobilizing the cells on the anisotropic scaffold. In another embodiment, the method further comprises the step of peeling off the textile template from the cellularized anisotropic scaffold before implanting the cellularized anisotropic scaffold in the subject. In yet another embodiment, the cells are myocytes. In yet another embodiment, the subject is human.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 1, comprising

FIG. 2, comprising

FIG. 3, comprising

FIG. 5, comprising Panels 5A-5F, illustrates ultra-structural analysis under SEM. Panels 5A and 5D: BIONATE® resin electrospun on flat copper target (BIONATE®_TG). Panels 5B and 5E: BIONATE® resin electrospun on cotton fabric (BIONATE®_CT). Panels 5C and 5F: BIONATE® resin electrospun on polyester fabric (BIONATE® PE). The bar represents 100 µm.

FIG. 9 is a bar graph illustrating fiber diameter of PGE 241 nanofibrous scaffolds.

FIG. 10, comprising

DETAILED DESCRIPTION OF THE INVENTION

Figure 1A:
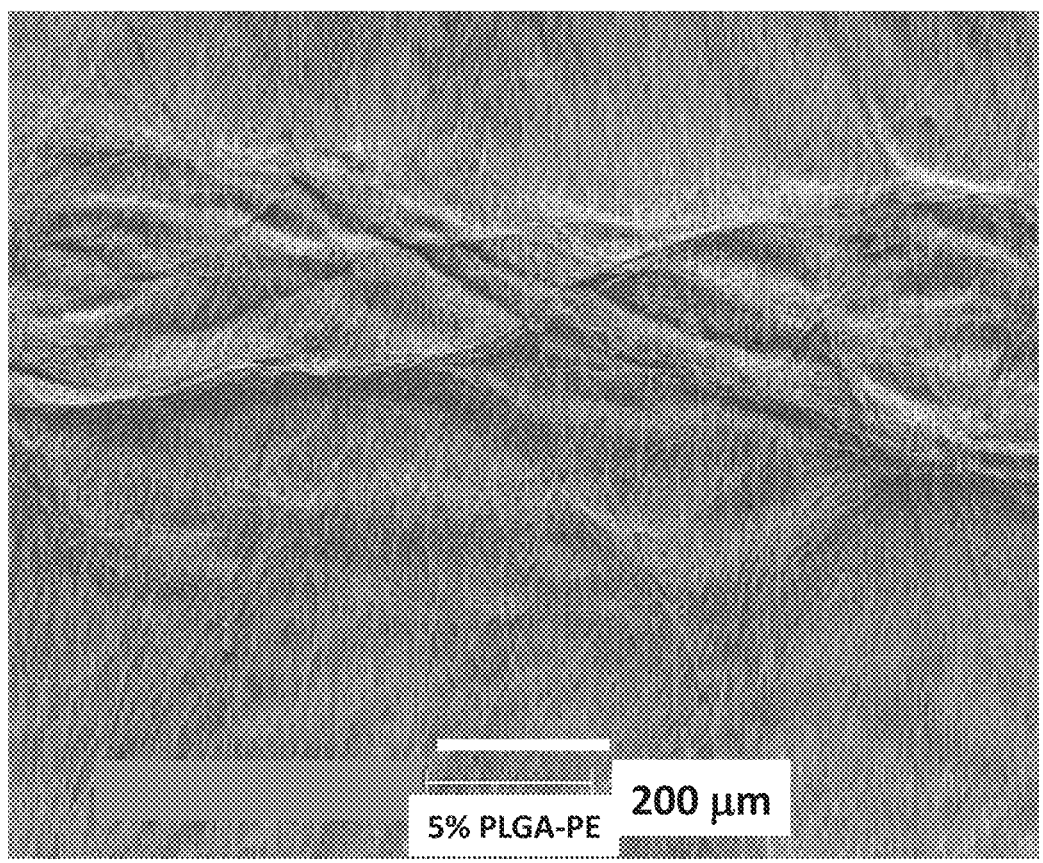
FIGS. 1A-1C, illustrates the ultrastructure of PLGA scaffold determined by scanning electron microscopy: PLGA_PE (FIG. 1A), PLGA_CT (FIG. 1B) and PLGA_TG (FIG. 1C). The original magnification was 100×, and the bar represents 200 µm in all figures.

The present invention relates to the unexpected discovery that a novel anisotropic scaffold for tissue engineering may be prepared by electrospinning a nanofibrous matrix material onto a textile template, whereby a complex-patterned, three-dimensional scaffold that mimics the basic anisotropic structure of a mammalian tissue is formed. The mechanical properties of this anisotropic three-dimensional scaffold may be modified depending on the characteristics of the textile template. The scaffolds of the invention are biocompatible and promote the proliferation and tissue-like anisotropic organization of cells of interest.

Definitions

As used herein, each of the following terms has the meaning associated with it in this section.

As used herein, unless defined otherwise, all technical and scientific terms generally have the same meaning as commonly understood by one of ordinary skill in the art to which this invention belongs. Generally, the nomenclature used herein and the laboratory procedures in cell culture, textile science, organic chemistry, and peptide chemistry are those well known and commonly employed in the art.

As used herein, the articles "a" and "an" refer to one or to more than one (i.e. to at least one) of the grammatical object of the article. By way of example, "an element" means one element or more than one element.

As used herein, the term "about" will be understood by persons of ordinary skill in the art and will vary to some extent on the context in which it is used. As used herein, "about" when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used herein, the term "PLGA" refers to poly(L-lactide-co-glicolide), also known as poly(L-lactic acid-co-glycolic acid).

As used herein, the term "HFP" refers to 1,1,1,3,3,3-hexafluoro-2-propanol.

As used herein, the term "SEM" refers to scanning electron microscopy.

As used herein, the term "PGE" refers to a blend of PLGA, gelatin and elastin.

As used herein, the term "conductive polymer" or "intrinsically conducting polymer" refers to an organic polymer that conducts electricity. Such compound may have metallic conductivity or be semiconductor. Non-limiting examples of conductive polymers include polyfluorenes, polyphenylenes, polypyrenes, polyazulenes, polynaphthalenes, polypyrroles, polycarbazoles, polyindoles, polyazepines, polyanilines (PANI), polythiophenes (PT), poly(3,4-ethylenedioxythiophene) (PEDOT), poly(p-phenylene sulfide) (PPS), polyacetylenes (PAC), poly(p-phenylene vinylene) (PPV), and combinations and copolymers thereof.

As used herein, the term "protein," and any term used to define a specific protein or class of proteins further includes, but is not limited to, fragments, analogs, conservative amino acid substitutions, non-conservative amino acid substitutions and substitutions with non-naturally occurring amino acids with respect to a protein or type or class of proteins. Thus, for example, collagen includes, but is not limited to, fragments, analogs, conservative amino acid substitutions, and substitutions with non-naturally occurring amino acids or residues with respect to any type or class of collagen.

As used herein, the term "residue" refers to an D- or L-amino acid or an amino acid mimetic that is incorporated into a protein by an amide bond. As such, the residue may be a naturally occurring amino acid or, unless otherwise limited, may encompass known analogs of natural amino acids that function in a manner similar to the naturally occurring amino acids (i.e., amino acid mimetics). Moreover, an amide bond mimetic includes peptide backbone modifications well known to those skilled in the art. Furthermore, one of skill in the art will recognize that, as mentioned above, individual substitutions, deletions or additions which alter, add or delete a single amino acid or a small percentage of amino acids (preferably less than 10%, more preferably less than 5%) in an encoded sequence are conservatively modified variations where the alterations result in the substitution of an amino acid with a chemically similar amino acid.

As used herein, the term "patient" or "subject" refers to a human or a non-human mammal. Non-human mammals include, for example, livestock and pets, such as ovine, bovine, porcine, canine, feline and murine mammals. Preferably, the patient or subject is human.

As used herein, the terms "implanted" and "implantation" as related to a subject in need thereof refer to an act of delivering a scaffold of the invention to a site within the subject and/or affixing the scaffold to the site within the subject.

Compositions of the Invention

The invention includes a composition comprising an anisotropic scaffold, which is generated by electrospinning a solution of matrix material upon a textile template. The composition of the invention finds use in tissue engineering and regenerative medicine.

Matrix Material Used within the Invention:

The matrix material useful within the scaffold is able to form a stable three-dimensional structure, on which cells may grow.

In one embodiment, the matrix material comprises a protein. Non-limiting examples of proteins contemplated within the invention are gelatin, collagen, fibrin, elastin, laminin, proteoglycans and fibronectin. More preferably, the protein is collagen of any type. The invention includes the various isoforms that are commonly recognized to exist within various families of proteins and other molecules. There are multiple types of each of these proteins and molecules that are naturally-occurring, as well as types that may be or are synthetically manufactured or produced by genetic engineering. For example, collagen occurs in many forms and types and all of these types and subsets are encompassed herein.

In another embodiment, the matrix material comprises a polymer. The polymers contemplated with the invention include, but are not limited to, the following: poly(urethane), poly(siloxane) or silicone, poly(ethylene), poly(vinyl pyrrolidone), poly(-hydroxy ethyl methacrylate), poly(N-vinyl pyrrolidone), poly(methyl methacrylate), poly(vinyl alcohol), poly(acrylic acid), polyacrylamide, poly(ethylene-co-vinyl acetate), poly(ethylene glycol), poly(methacrylic acid), polylactide (PLA), polyglycolide (PGA), poly(lactide-co-glycolide) (also known as poly(L-lactic acid-co-glycolic acid; PLGA), polyanhydride, polyorthoester, polycarbonate, and mixtures and co-polymer thereof, or any other similar synthetic polymers that may be developed that are biologically compatible. In one embodiment, the polymer is PLGA. In another embodiment the polymer is polycarbonate urethane.

The polymer compositions used to make the biodegradable scaffold are preferably biocompatible. By "biocompatible," it is meant that a polymer composition and its normal degradation products in vivo are cytocompatible and are substantially non-toxic and non-carcinogenic in a patient within useful, practical and/or acceptable tolerances.

The term "biocompatible polymer" shall also include co-polymers and blends, and any other combinations of the forgoing either together or with other polymers generally.

By "cytocompatible," it is meant that the polymer composition may sustain a population of cells and/or the polymer composition or device, and degradation products thereof are not cytotoxic and/or carcinogenic within useful, practical and/or acceptable tolerances. For example, the polymer when placed in a human myocardial cell culture does not adversely affect the viability, growth, adhesion, and number of cells. In another non-limiting example, the polymer, when implanted in a patient, does not cause a substantial adverse reaction or substantial harm to cells and tissues in the body. For instance, the polymer composition or device does not cause necrosis, inflammation, an immune response or an infection resulting in harm to tissues from the implanted scaffold. In one non-limiting embodiment, the polymer composition or device is "biocompatible" to the extent they are acceptable for use in a human or veterinary patient in accordance with applicable governmental regulatory provisions, such as, without limitation, those of the U.S. Food and Drug Administration.

In a non-limiting embodiment, the polymer composition is selected so that it degrades in situ on a timescale that is similar to an expected rate of healing of the tissue damage or repair. Non-limiting examples of useful in situ degradation rates include between one week and one year, between two weeks and ten months, and between one month and six months or increments therebetween. When the polymer is used to treat a patient after a myocardial infarction, it may be advantageous to tailor the polymer degradation rate to the size of the infarction as determined by methods such as echocardiography or magnetic resonance imaging. For example, when the size of the infarction is large, it would be advantageous to select a more slowly degrading polymer, so that the entire infarction has a chance to heal before the polymer completely degrades.

Solvent Used in the Preparation of the Matrix Material Solution:

In order to allow the matrix material to be electrospun onto the textile template, the matrix material should be first dissolved in an appropriate solvent. Any solvent that allows delivery of the matrix material to the electrospinning equipment may be used. The solvent may be used for dissolving or suspending the matrix material to be electrospun. Solvents useful for dissolving or suspending a material or a substance depend on the material or substance. For example, collagen may be electrospun as a solution or suspension in water, 2,2,2-trifluoroethanol, 1,1,1,3,3,3-hexafluoro-2-propanol (also known as hexafluoroisopropanol or HFP), or combinations thereof. For example, fibrin monomer may be electrospun from solvents such as urea, monochloroacetic acid, water, 2,2,2-trifluoroethanol, HFP, or combinations thereof. For example, elastin may be electrospun as a solution or suspension in water, 2,2,2-trifluoroethanol, isopropanol, HFP, or combinations thereof, such as isopropanol and water. As a non-limiting example, elastin is electrospun from a solution of 70% isopropanol and 30% water containing 250 mg/ml of elastin. Other lower order alcohols, especially halogenated alcohols, may also be used. Other solvents that may be used or combined with other solvents in electrospinning natural matrix materials include acetamide, N-methylformamide, N,N-dimethylformamide (DMF), dimethylsulfoxide (DMSO), dimethylacetamide, N-methyl pyrrolidone (NMP), acetic acid, trifluoroacetic acid, ethyl acetate, acetonitrile, trifluoroacetic anhydride, 1,1,1-trifluoroacetone, maleic acid, and hexafluoroacetone.

Proteins and peptides associated with membranes are often hydrophobic and thus do not dissolve readily in aqueous solutions. Such proteins may be dissolved in organic solvents such as methanol, chloroform, and trifluoroethanol (TFE) and emulsifying agents. Any other solvents known to those skilled in the protein chemical art may be used, for example solvents useful in chromatography, especially high performance liquid chromatography. Proteins and peptides are also soluble, for example, in HFP, hexafluoroacetone, chloroalcohols in conjugation with aqueous solutions of mineral acids, dimethylacetamide containing 5% lithium chloride, and in acids such as acetic acid, hydrochloric acid and formic acid. In some embodiments, the acids are very dilute, in others the acids are concentrated. N-methyl-morpholine-N-oxide may also be used with many polypeptides. Other examples, used either alone or in combination with organic acids or salts, include the following: triethanolamine, dichloromethane, methylene chloride, 1,4-dioxane, acetonitrile, ethylene glycol, diethylene glycol, ethyl acetate, glycerine, propane-1,3-diol, furan, tetrahydrofuran, indole, piperazine, pyrrole, pyrrolidone, 2-pyrrolidone, pyridine, quinoline, tetrahydroquinoline, pyrazole and imidazole. Combinations of solvents may also be used.

Synthetic polymers may be electrodeposited from, for example, HFP, methylene chloride, ethyl acetate, acetone, 2-butanone (methyl ethyl ketone), diethyl ether, ethanol, cyclohexane, water, dichloromethane (methylene chloride), tetrahydrofuran, dimethylsulfoxide (DMSO), acetonitrile, methyl formate, and solvent mixtures thereof. In one embodiment, HFP or methylene chloride is used.

Selection of a solvent will depend upon the characteristics of the synthetic polymer to be electrodeposited, such as the secondary forces that stabilize polymer-polymer interactions and the solvent's ability to replace these with strong polymer-solvent interactions. In the case of polypeptides such as collagen, and in the absence of covalent cross-linking, the principal secondary forces between chains are: (1) Coulombic, resulting from attraction of fixed charges on the backbone and dictated by the primary structure (e.g., lysine and arginine residues will be positively charged at physiological pH, while aspartic or glutamic acid residues will be negatively charged); (2) dipole-dipole, resulting from interactions of permanent dipoles—the hydrogen bond, commonly found in polypeptides, is the strongest of such interactions; and (3) hydrophobic interactions, resulting from association of non-polar regions of the polypeptide due to a low tendency of non-polar species to interact favorably with polar water molecules.

Therefore, solvents or solvent combinations that may favorably compete for these interactions may dissolve or disperse polypeptides. For example, HFP and TFE possess a highly polar hydroxyl group adjacent to a very hydrophobic fluorinated region. While not wishing to be bound by theory, it is believed that the alcohol portion may hydrogen bond with peptides, and may also solvate charges on the backbone, thus reducing Coulombic interactions between molecules. Additionally, the hydrophobic portions of these solvents may interact with hydrophobic domains in polypeptides, helping to resist the tendency of the latter to aggregate via hydrophobic interactions. Solvents such as HFP and TFE, due to their lower overall polarities compared to water, may not compete well for intramolecular hydrogen bonds that stabilize secondary structures such as an alpha helix. Consequently, alpha helices in these solvents are believed to be stabilized by virtue of stronger intramolecular hydrogen bonds. The stabilization of polypeptide secondary structures in these solvents is believed to be desirable, especially in the cases of collagen and elastin, to preserve the proper formation of collagen fibrils during electrospinning. In some embodiments, solvents are selected based on their tendency to induce helical structure in electrospun protein fibers, thereby predisposing monomers of collagen or other proteins to undergo polymerization and form helical polymers that mimic the native collagen fibril. Examples of such solvents include halogenated alcohols, preferably fluorinated alcohols (HFP and TFE), hexafluoroacetone, chloroalcohols in conjugation with aqueous solutions of mineral acids and dimethylacetamide, preferably containing lithium chloride. HFP and TFE are more preferred. In some embodiments, water is added to the solvents.

Additionally, it is often desirable, although not necessary, for the solvent to have a relatively high vapor pressure to promote the stabilization of an electrospinning jet to create a fiber as the solvent evaporates. A relatively volatile solvent is also desirable to minimize coalescence of droplets during and after spraying and formation of dry electrospun materials. In embodiments involving higher boiling point solvents, it is often desirable to facilitate solvent evaporation by warming the spinning or spraying solution, and optionally the electrospinning itself, or by electrospinning in reduced atmospheric pressure. It is also believed that creation of a stable jet resulting in a fiber is facilitated by a low surface tension of the polymer/solvent mixture, and this may guide solvent choice as well.

In functional terms, solvents used for electrospinning have the principal role of creating a mixture with collagen and/or other materials to be electrospun. The concentration of a given solvent is often an important consideration in determining the type of electrospinning that will occur. In electrospinning, interactions between molecules of electroprocessed material stabilize the jet, leading to fiber formation. For electrospinning, the solvent should sufficiently dissolve or disperse the polymer to prevent the jet from disintegrating into droplets and should thereby allow formation of a stable jet in the form of a fiber. Viscosity increases as concentration of a polymer or other material to be electroprocessed increases. Above a critical concentration associated with extensive chain entanglements of materials, however, the viscosity will increase more rapidly with concentration, as opposed to a more gradual, linear rise with concentration at lower concentrations. Departures from linearity approximately coincide with the transition from electrospraying to electrospinning.

Electrospinning:

The matrix material may be deposited on the textile template using electrospinning. This platform technology is widely used to fabricate scaffolds composed of nano- and micro-fibrous architecture in tissue engineering (Li et al., 2006, Biomaterials 27(13):2705-15; Li et al., 2005, Biomaterials 26(30):5999-6008). The process of electrospinning involves placing a polymer-containing fluid (for example, a polymer solution, polymer suspension, or polymer melt) in a reservoir equipped with a small orifice, such as a needle or pipette tip and a metering pump. One electrode of a high voltage source is placed in electrical contact with the polymer-containing fluid or orifice, while the other electrode is placed in electrical contact with a target (typically a collector screen or rotating mandrel). During electrospinning, the polymer containing fluid is charged by the application of high voltage to the solution or orifice (for example, about 3 to about 15 kV) and then forced through the small orifice by the metering pump, providing a steady flow. While the polymer-containing fluid at the orifice normally would have a hemispherical shape due to surface tension, the application of the high voltage causes the otherwise hemispherically shaped polymer-containing fluid at the orifice to elongate to form a conical shape known as a Taylor cone. With sufficiently high voltage applied to the polymer-containing fluid and/or orifice, the repulsive electrostatic force of the charged polymer-containing fluid overcomes the surface tension and a charged jet of fluid is ejected from the tip of the Taylor cone and accelerated towards the target, which typically is biased between −2 to −10 kV. A focusing ring with an applied bias (for example, 1 to 10 kV) may be optionally used to direct the trajectory of the charged jet of polymer-containing fluid. As the charged jet of fluid travels towards the biased target, it undergoes a complicated whipping and bending motion. If the fluid is a polymer solution or suspension, the solvent typically evaporates during mid-flight, leaving behind a polymer fiber on the biased target. If the fluid is a polymer melt, the molten polymer cools and solidifies in mid-flight and is collected as a polymer fiber on the biased target. As the polymer fibers accumulate on the biased target, a porous mesh is formed on the biased target.

The properties of the electrospun matrix described herein may be tailored by varying the electrospinning conditions. For example, when the template is relatively close to the orifice, the resulting electrospun mesh tends to contain unevenly thick fibers, such that some areas of the fiber have a "bead-like" appearance. However, as the template is moved further away from the orifice, the fibers of the mesh tend to be more uniform in thickness. Moreover, the template may be moved relative to the orifice. In certain embodiments, the template is moved back and forth in a regular and periodic fashion, such that fibers of the mesh are substantially parallel to each other. When this is the case, the resulting mesh may have a higher resistance to strain in the direction parallel to the fibers, compared to the direction perpendicular to the fibers. In other embodiments, the biased target is moved relative to the orifice in a two- or three-dimensional pattern to create a mesh comprising one or more patterned layers with similar or different strand orientation, thickness, etc. In other embodiments, the template is moved randomly relative to the orifice, so that the resistance to strain in the plane of the mesh is isotropic. The properties of the electrospun matrix may also be varied by changing the magnitude of the voltages applied to the electrospinning system. In a non-limiting example, the electrospinning apparatus includes an orifice biased to 20 kV. In another non-limiting example, the electrospinning apparatus includes a template biased to −7 kV. In yet another non-limiting example, the electrospinning apparatus includes a focusing ring biased to 3 kV.

In one embodiment, the polymer is co-span with at least one compound selected from the group consisting of gelatin, elastin and mixtures thereof. In another embodiment, the polymer is poly(lactide-co-glycolide) and it is co-span with gelatin and elastin.

In one embodiment, the polymer is co-span with at least one conductive polymer. The conductive polymer contemplated within the invention may be selected from the group consisting of polyfluorene, polyphenylene, polypyrene, polyazulene, polynaphthalene, polypyrrole, polycarbazole, polyindole, polyazepine, polyaniline, polythiophene, poly(3,4-ethylenedioxythiophene), poly(p-phenylene sulfide), polyacetylene, poly(p-phenylene vinylene), and combinations and co-polymers thereof. In one embodiment, the conductive polymer is selected from the group consisting of polyaniline, polypyrrole and poly(3,4-ethylenedioxythiophene). In a non-limiting aspect, co-spinning of a non-conductive polymer with a conductive polymer allows for generation of a material with electrical conductance similar to that of the cardiac muscle tissue.

Template Used in Electrospinning:

The template useful within the invention is a textile template. In one embodiment, the textile template is a knitted fabric. In another embodiment, the textile template is a woven fabric. By using knitted or woven fabrics as a template in the electrospinning system, it is possible to obtain three-dimensional scaffolds with distinct patterns and varying degrees of anisotropies.

The textile used within the invention may be any textile that is compatible with the matrix material and the solvent used in the preparation of the scaffold of the invention. In one embodiment, the textile is cotton. In another embodiment, the textile is polyester. Properties of the textile that may influence its properties as a template are, for example, yarn number, weight, thickness, fabric structure and fabric construction.

In one embodiment, the yarn number of the textile varies from about 15 tex to about 75 tex. In another embodiment, the yarn number of the textile varies from about 20 tex to about 60 tex. In yet another embodiment, the weight of the textile varies from about 100 g/m$^2$ to about 300 g/m$^2$. In yet another embodiment, the thickness of the textile varies from about 0.8 mm to about 1.2 mm. In yet another embodiment, the thickness of the textile varies from about 0.9 mm to about 1.1 mm. In yet another embodiment, the fabric structure of the textile is Jersey (plain weft) knitted fabric. In yet another embodiment, the fabric construction of the textile varies from about 6 wale/cm to about 10 wale/cm. In yet another embodiment, the fabric construction of the textile varies from about 6 course/cm to about 8 course/cm.

In one embodiment, after the matrix material is deposited on the textile template, the textile template is peeled off, resulting in a textile-free scaffold. In another embodiment, after the matrix material is deposited on the textile template, the scaffold is submitted to further manipulation as required by its ultimate use as an implant, and only before the implantation takes place is the textile template peeled off. In yet another embodiment, after the matrix material is deposited on the template, the scaffold is submitted to further manipulation as required by its ultimate use as an implant, and the resulting material is implanted in the subject without the textile template being peeled off.

Manipulation of the Scaffold:

In one aspect, once formed, the scaffold may be derivatized with cells. Cells may be micro-integrated with the scaffold using a variety of methods. The cells are then allowed to proliferate on the surface and interstices of the scaffold. In one embodiment, the scaffold may be treated with a protein, such as collagen, and then seeded with cells. In another embodiment, the scaffold may be submersed in an appropriate growth medium for the cells of interest, and then exposed to the cells. The scaffold is then removed from the growth medium, washed if necessary, and implanted in a patient. In yet another embodiment, the cells may be placed in a suitable buffer or liquid growth medium and drawn onto and/or into the scaffold by using vacuum filtration. In yet another embodiment, the cells of interest are suspended into an appropriate solution (e.g., a growth medium or buffer) and then sprayed onto a scaffold while the scaffold is being formed by electrospinning.

By way of example only, the cells that may be incorporated onto or into the biodegradable scaffold include stem cells, precursor cells, smooth muscle cells, skeletal myoblasts, myocardial cells, endothelial cells, and genetically modified cells. In one embodiment, the genetically modified cells are capable of expressing a therapeutic substance, such as a growth factor. Non-limiting examples of therapeutic agents useful within the invention that may be expressed by cells are a neurotrophic factor, such as nerve growth factor, brain-derived neurotrophic factor, neurotrophin-3, neurotrophin-4, neurotrophin-5, and ciliary neurotrophic factor; a growth factor, such as basic fibroblast growth factor (bFGF), acidic fibroblast growth factor (aFGF), vascular endothelial growth factor (VEGF), hepatocyte growth factor (HGF), insulin-like growth factors (IGF), platelet derived growth factor (PDGF), transforming growth factor-beta (TGF-(3), pleiotrophin protein (neurite growth-promoting factor 1), and midkine protein (neurite growth-promoting factor 2); an antiinflammatory cytokine; and an anti-inflammatory protein.

Implantation of the Scaffold of the Invention

The scaffold of the invention may be delivered to the subject by any surgical procedure, including minimally invasive techniques, such as laparoscopic surgery, as well as invasive techniques such as thoracic surgery or open heart surgery. The site of the implant may be, for example and without limitation, inside the heart, on the outer surface of the heart, or may connect the inner and outer surfaces of the heart. The site may be either on or near the tissue that is damaged or deficient. In a non-limiting example, when the scaffold of the invention is used to treat a patient after sub-acute myocardial infarction, the scaffold is implanted over the infarcted region. The scaffold may be any useful shape including regular geometric shapes (e.g., circle, square, etc.) or irregular shapes. Often, it is useful to determine the required size of the construct prior to the surgery, by using an imaging technique, non-limiting examples of which include echocardiography and magnetic resonance imaging. Furthermore, the construct may be designed to possess anisotropic mechanical properties and then specifically oriented in a particular direction with respect to the surrounding tissue (e.g., heart muscle) prior to implantation.

The construct comprising the scaffold of the invention may be affixed to the site by any method known in the art. The construct comprising the scaffold of the invention may be implanted by using any surgical fasteners, non-limiting examples of which include sutures, staples, or adhesives, such as fibrin-based adhesives, for example. In one non-limiting embodiment, the construct is attached to the left ventricular surface of the heart following myocardial infarction by using sutures. When applying the construct to the surface of the heart, it may often be advantageous to gently scrape the surface of the heart to be covered (e.g., an infarcted region) prior to implantation in order to cause slight bleeding and the formation of a blood clot. It may also be advantageous to suture the construct while the construct is under a slight amount of tension.

Methods of the Invention

The invention includes a method of preparing an anisotropic scaffold. The method comprises the step of electrospinning a solution of matrix material in a solvent upon a textile template to form the anisotropic scaffold.

The invention also includes a method of preparing a cellularized anisotropic scaffold. The method comprises the step of electrospinning a solution of matrix material in a solvent upon a textile template to form an anisotropic scaffold. The method further comprises the optional step of coating the anisotropic scaffold with collagen. The method further comprises the step of immobilizing cells on the anisotropic scaffold to form the cellularized anisotropic scaffold.

The invention further comprises a method of implanting a cellularized anisotropic scaffold in a subject in need thereof. The method comprises the step of electrospinning a solution of matrix material in a solvent upon a textile template to form an anisotropic scaffold. The method further comprises the optional step of coating the anisotropic scaffold with collagen. The method further comprises the step of immobilizing cells on the anisotropic scaffold to form the cellularized anisotropic scaffold. The method further comprises the optional step of implanting the cellularized anisotropic scaffold in the subject.

In one embodiment, the matrix material comprises a protein. In another embodiment, the matrix material comprises a polymer. In yet another embodiment, the polymer may be selected from the group consisting of poly(urethane), poly(siloxane), poly(ethylene), poly(vinyl pyrrolidone), poly(2-hydroxy ethyl methacrylate), poly(N-vinyl pyrrolidone), poly(methyl methacrylate), poly(vinyl alcohol), poly(acrylic acid), polyacrylamide, poly(ethylene-co-vinyl acetate), poly(ethylene glycol), poly(methacrylic acid), polylactide, polyglycolide, poly(lactide-co-glycolide), polyanhydride, polyorthoester, polycarbonate, and combinations and co-polymers thereof. In yet another embodiment, the polymer is poly(lactide-co-glycolide). In yet another embodiment, the polymer is polycarbonate urethane.

In one embodiment, the polymer is co-span with at least one compound selected from the group consisting of gelatin, elastin and mixtures thereof. In another embodiment, the polymer is poly(lactide-co-glycolide) and the polymer is co-span with gelatin and elastin.

In one embodiment, the polymer is co-span with at least one conductive polymer. In another embodiment, the conductive polymer is selected from the group consisting of polyfluorene, polyphenylene, polypyrene, polyazulene, polynaphthalene, polypyrrole, polycarbazole, polyindole, polyazepine, polyaniline, polythiophene, poly(3,4-ethylenedioxythiophene), poly(p-phenylene sulfide), polyacetylene, poly(p-phenylene vinylene), and combinations and co-polymers thereof. In yet another embodiment, the conductive polymer is selected from the group consisting of polyaniline, polypyrrole and poly(3,4-ethylenedioxythiophene). In yet another embodiment, the polymer is polycarbonate urethane.

In one embodiment, the matrix material is biocompatible and cytocompatible.

In one embodiment, the solvent is selected from the group consisting of water, urea, methylene chloride, cyclohexane, diethyl ether, 1,4-dioxane, furan, tetrahydrofuran, ethanol, isopropanol, propane-1,3-diol, ethylene glycol, diethylene glycol, glycerine, acetone, 2-butanone, ethyl acetate, methyl formate, acetonitrile, acetamide, dimethylacetamide, N-methylformamide, N,N-dimethylformamide, N-methyl pyrrolidone, N-methyl morpholine-N-oxide, dimethylsulfoxide, formic acid, acetic acid, hydrochloric acid, maleic acid, 1,1,1-trifluoroacetone, hexafluoroacetone, 2,2,2-trifluoroethanol, 1,1,1,3,3,3-hexafluoro-2-propanol, monochloroacetic acid, trifluoroacetic acid, trifluoroacetic anhydride, triethanolamine, indole, piperazine, pyrrole, 2-pyrrolidone, pyridine, quinoline, tetrahydroquinoline, pyrazole, imidazole, and combinations thereof. In another embodiment, the solvent is 1,1,1,3,3,3-hexafluoro-2-propanol.

In one embodiment, the textile template is a knitted fabric. In another embodiment, the textile template is a woven fabric. In yet another embodiment, the textile template is polyester or cotton. In yet another embodiment, the yarn number of the textile varies from about 15 tex to about 75 tex. In yet another embodiment, the yarn number of the textile varies from about 20 tex to about 60 tex. In yet another embodiment, the weight of the textile varies from about 100 g/m$^2$ to about 300 g/m$^2$. In yet another embodiment, the thickness of the textile varies from about 0.8 mm to about 1.2 mm. In yet another embodiment, the thickness of the textile varies from about 0.9 mm to about 1.1 mm. In yet another embodiment, the fabric structure of the textile is Jersey (plain weft) knitted fabric. In yet another embodiment, the fabric construction of the textile varies from about 6 wale/cm to about 10 wale/cm. In yet another embodiment, the fabric construction of the textile varies from about 6 course/cm to about 8 course/cm.

In one embodiment, the method of the invention further comprises the step of peeling off the textile template from the anisotropic scaffold.

In one embodiment, the method of the invention further comprises the step of peeling off the textile template from the anisotropic scaffold before immobilizing the cells on the anisotropic scaffold. In another embodiment, the method of the invention further comprises the step of peeling off the textile template from the cellularized anisotropic scaffold before implanting the cellularized anisotropic scaffold in the subject.

In yet one embodiment, the cells are myocytes. In another embodiment, the subject is human.

It is contemplated that any embodiment discussed in this specification may be implemented with respect to any method or composition of the invention, and vice versa. Furthermore, compositions of the invention may be used to achieve methods of the invention.

Those skilled in the art will recognize, or be able to ascertain using no more than routine experimentation, numerous equivalents to the specific procedures, embodiments, claims, and examples described herein. Such equivalents are considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that, wherever values and ranges are provided herein, the description in range format is merely for convenience and brevity and should not be construed as an inflexible limitation on the scope of the invention. Accordingly, all values and ranges encompassed by these values and ranges are meant to be encompassed within the scope of the present invention. Moreover, all values that fall within these ranges, as well as the upper or lower limits of a range of values, are also contemplated by the present application. The description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Materials and Methods

Materials Used in the Studies.

Poly(L-lactide-co-glycolide) (PLGAPURASORB® 1.24 kg/1) was purchased from PURAC Biomaterials (Gorinchem, The Netherlands). Fabrics made from polyester and cotton were obtained from Philadelphia University, Department of Engineering &Textiles (Philadelphia, Pa.), and their characteristics are summarized in Table 1.

TABLE 1

Properties of fabrics.

|  | yellow | white |
|---|---|---|
| Type of fibers | cotton | polyester |
| Yarn number | 57.17 tex | 21.24 tex |
| Weight | 218.11 g/m² | 142.39 g/m² |
| Thickness | 0.935 mm | 1.029 mm |
| Fabric structure | Jersey (plain weft) knitted fabric | Jersey (plain weft) knitted fabric |
| Fabric construction | 7 wale/cm, 8 course/cm | 8.5 wale/cm, 16 course/cm |

Electrospinning.

For electrospinning onto a textile template, a home-made horizontal electrospinning setup was selected (Li et al., 2006, Biomaterials 27(13):2705-15; Li et al., 2005, Biomaterials 26(30):5999-6008).

For the initial studies, 5% PLGA was dissolved in 1,1,1,3,3,3-hexafluoro-2-propanol (HFP, Sigma-Aldrich, St Louis, Mo.) for 24 hours. Polyester and cotton fabrics (8 cm²) were mounted on a polycarbonate frame and stretched 50% biaxial and uniaxial directions on a frame, respectively, which was placed in front of rectangular (10 cm²) copper target.

In preliminary experiments, electrospinning parameters were optimized to obtain uniform bead-less fibers with average diameters of ~300 nm. The distance between the textile and needle was 15 cm, the syringe pump flow rate was 0.5 ml/h, and applied voltage was 20 kV. Under these conditions it took ~8 hrs to spin a 10 cm×10 cm×0.15 mm scaffold of PLGA fibers onto the various templates of polyester (PE), cotton (CT) fabric and the copper target itself. The samples were peeled off from the textile templates and the copper target, respectively for further use.

Ultrastructure of Scaffolds.

PLGA scaffolds and fabrics were cut into circular pieces (d~0.5 mm) and coated with Pt/Pd for 40 seconds with a gas pressure of 0.025 mbar, and the current during the coating was 40 mA. The ultra-structure of the samples was characterized by scanning electron microscopy (SEM, XL-30 Environmental SEM-FEG or Zeiss Supra 50VP) using an acceleration voltage of 10.0 kV.

Mechanical Testing.

Dry samples were cut into rectangular pieces (0.5 cm×2.5 cm) and their weights were measured. Wet samples were cut into pieces (3 mm×15 mm). Tensile properties of PLGA scaffolds were measured in three independent experiments by Instron 5500 (Norwood, Mass.). Each sample was analyzed in triplicate.

Cell Culture.

H9C2 rat cardiomyoblasts (a cardiac myocyte progenitor cell line) were cultured in DMEM (Dulbeccos's modified Eagle's medium; Gibco, Gland Island, N.Y.) high glucose supplemented with 10% FBS (fetal bovine serum), 2 mM L-glutamine, 1 mM sodium pyruvate, as previously described (Bidez et al., 2006, J. Biomater. Sci. Polym. Ed. 17(1-2):199-212).

Cell Proliferation.

ALAMARBLUE® dye (AdB Serotec, Raleigh, N.C.) was used for cell proliferation analysis. For each type of scaffold, PLGA_PE (PLGA spun on polyester fabric), PLGA_CT (PLGA spun on cotton fabric) and PLGA_TG (PLGA spun on flat target) and fabrics, three circular samples were placed in the bottom of a well of 24-well plates, secured with Vyton O-rings and sterilized with 10% ABAM (Antibiotic-Antimycotic Solution) and then hydrated in 1×PBS (Phosphate Buffered Saline) without calcium and magnesium for 12 hours.

The various PLGA scaffolds, textile fabric templates and control wells were coated with 1 mg/ml rat tail collagen-I (Sigma-Aldrich, St Louis, Mo.) for 30 minutes. 5×10⁴ cells were then seeded on the sterilized scaffolds, fabrics and control wells. After 2 hours, the scaffolds and textiles were transferred to a new 24-well plate to avoid counting cells that were attached on the bottom of the well plate. At various time points, 1 ml of 10% AB in cell medium was added to the each sample and placed in an incubator (5% $CO_2$, 37° C.). After 4 hours, 200 μL from each sample were transferred to a 96 well-plate to measure AB fluorescence in a fluorescence plate reader, as previously described (Li et al., 2005, Biomaterials 26(30):5999-6008). Cellularized samples were then fixed with 4% formaldehyde for 15 minutes and kept in 1×PBS without calcium and magnesium for cell imaging and analysis of the mechanical properties of wet and cellularized scaffolds.

Cell Imaging.

Cellularized scaffolds were first permeabilized with 0.2% Triton-X and then stained with 1 μg/ml bisbenzimide (BBZ, nuclear stain) and 1 µg/ml Rodhamine-phalloidin (F-actin stain) in 1×PBS with for 30 minutes. Following four washes in 1×PBS for 5 minutes each, the wet samples were analyzed in a confocal microscope (Mondrinos et al., 2007, Am. J. Physiol. Lung Cell Mol. Physiol. 293(3):L639-50).

Example 1

Scaffolds Manufacturing and Characterization

Figure 1B:
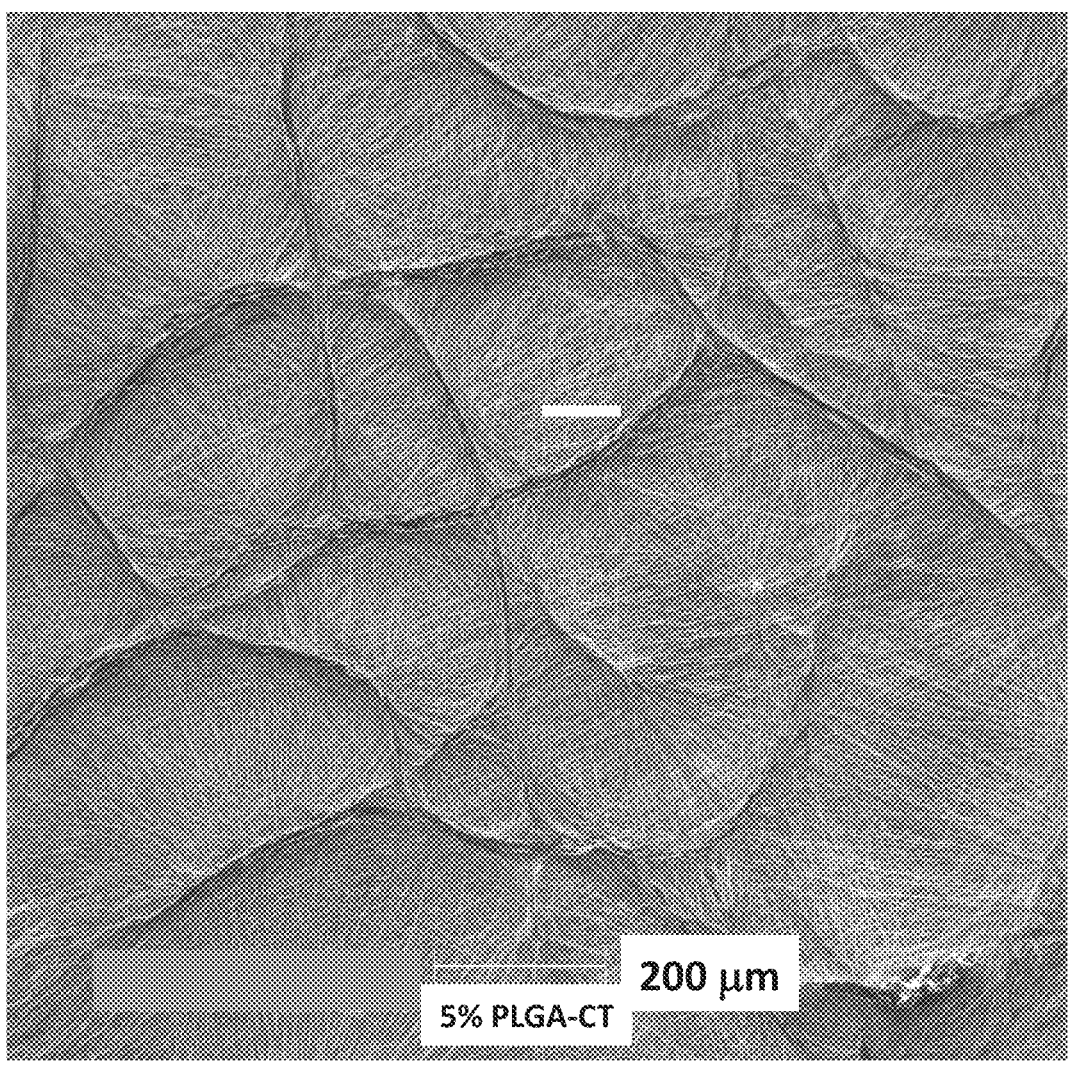
Figure 1C:
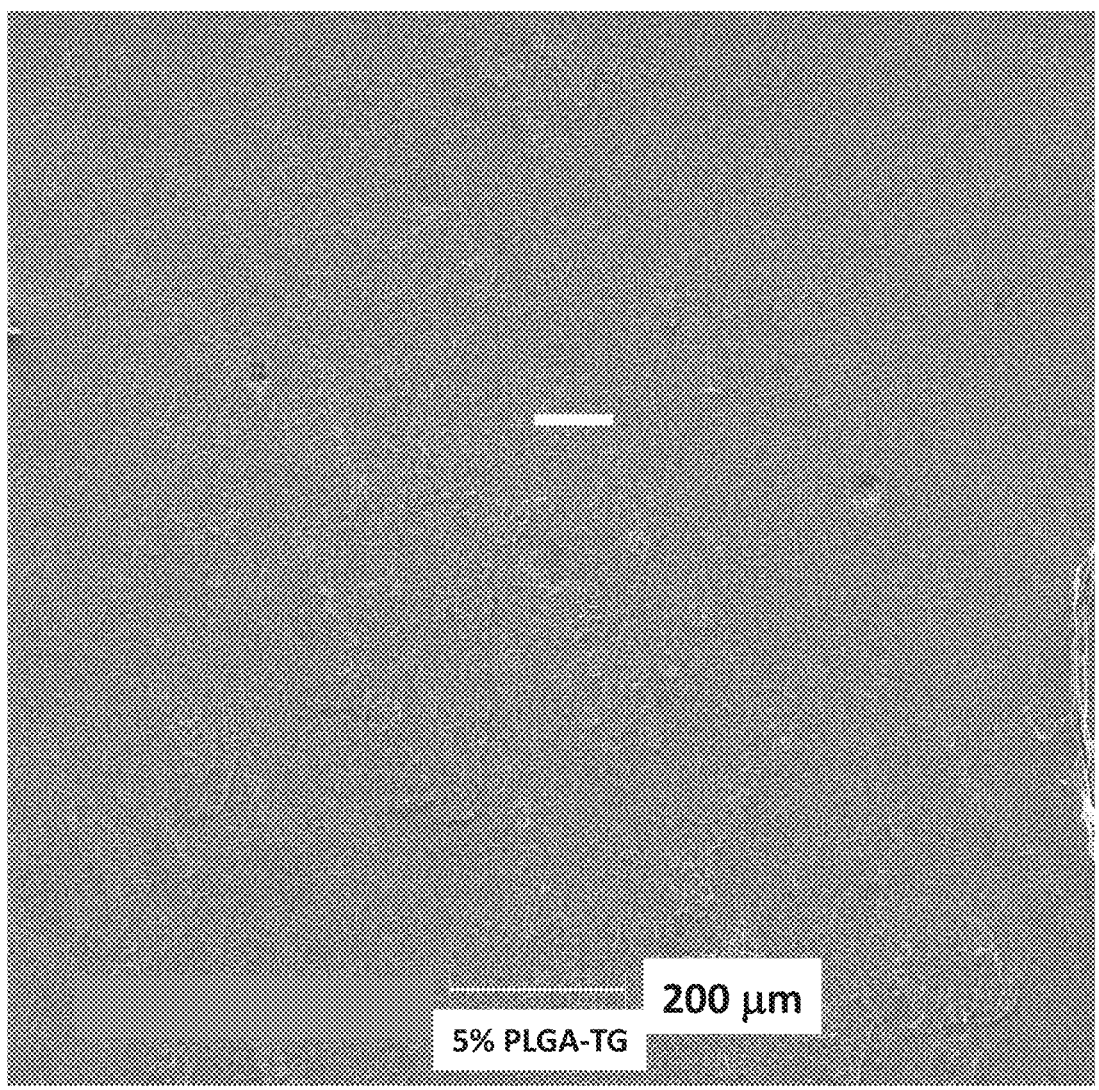

According to the SEM results, PLGA_TG was characterized by a flat surface consisting of a random mesh of non-oriented fibers that settled in the same plane. By contrast, textile-templated scaffolds exhibited distinct anisotropies and three-dimensional patterns according to the type of fabric template used to construct it. The patterning of PLGA_PE mimicked that of its template (polyester), whereas the patterns PLGA_CT bore little resemblance to those of the cotton templates. Moreover, and in contrast to scaffolds spun onto a flat target, both PLGA_PE and PLGA_CT textile-templated scaffolds exhibited regions where the fibers were aligned in parallel, indicating significant structural anisotropy (FIG. 1). Previously, parallel alignment of electrospun fibers was generally obtained by using mandrels spinning at high rpm (He et al., 2009, J. Biomed. Mater. Res. A 90(1):205-16). However, with the system herein described it is possible to generate aligned fibers in a variety of patterns according to the intrinsic geometries of the textile-templated scaffolds. This indicates that specific textile materials may serve as readily available templates for electrospinning and may yield anisotropic scaffolds with a variety of three-dimensional patterns, depending on the type and diameter of the yarn as well as the unique structure and morphology of the various textile templates. When comparing PE and CT templated scaffolds, fiber alignment and patterning was less pronounced on the PE templated scaffolds as was on the CT templated scaffolds.

The significant change and differences in the morphology of the various PLGA scaffolds may also lead to differences in their mechanical properties. To test this possibility, the Young's Moduli of the samples was measured using an Instron 5500 at 1 mm/min crosshead speed. Indeed, significant differences were identified in the mechanical properties of the various scaffolds based upon these measurements (Table 2).

TABLE 2

Fiber diameter and tensile testing results of the scaffolds.

| Sample | Fiber diameter (nm) | Young's modulus (MPa) | Young's modulus (MPa) (wet & cellularized scaffolds) |
|---|---|---|---|
| PLGA_TG | 287.8 ± 77.5 | 264.5 ± 44.8 | 389.6 ± 143.7 |
| PLGA_CT | 302.5 ± 67.6 | 141 ± 7.2 | 277.6 ± 85.6 |
| PLGA_PE | 254.3 ± 50.6 | 54.9 ± 12.6 | 245.4 ± 107.5 |

While fiber diameters between the three scaffolds were indistinguishable, the Young's moduli of both dry and wet textile-templated scaffolds were significantly lower than the Young's moduli of scaffolds directly spun onto smooth/flat targets. The lowest Young's moduli were measured in PE-templated scaffolds, which also exhibited the highest degree of anisotropy. This suggests that, by manipulating textile properties such as design, yarn size and type, scaffolds with distinct patterns/anisotropy and tunable mechanical properties may be manufactured. Given the nature of the biopolymer (PLGA) used in these studies, the mechanical properties of the anisotropic, patterned scaffolds did not match those of the myocardium. However, with the principles and concepts outlined herein, by using elastomeric polymers such as polyurethane, elastic properties suitable for the use of these patterned anisotropic scaffolds, as myocardial patches, may be achieved. As a major strength of the present approach, the platform technology of electrospinning nanofibrous scaffolds onto patterned textile templates allows for a simpler, faster and more efficient manufacturing of smart anisotropic scaffolds for use as cardiac patches or tissue repair compared to the current standard.

Example 2

Biocompatibility of Scaffolds

To assess cell attachment to and proliferation on the textile-templated three-dimensional PLGA scaffolds, the H9C2 cardiomyoblast cells were seeded at a density of $5 \times 10^4$ cells/ml onto patterned and flat scaffolds as well as on the "gold standard" i.e., grown on tissue culture plastic (TCP) surfaces in the bottom of 24 well plates and maintained in the culture for three days.

Figure 4:
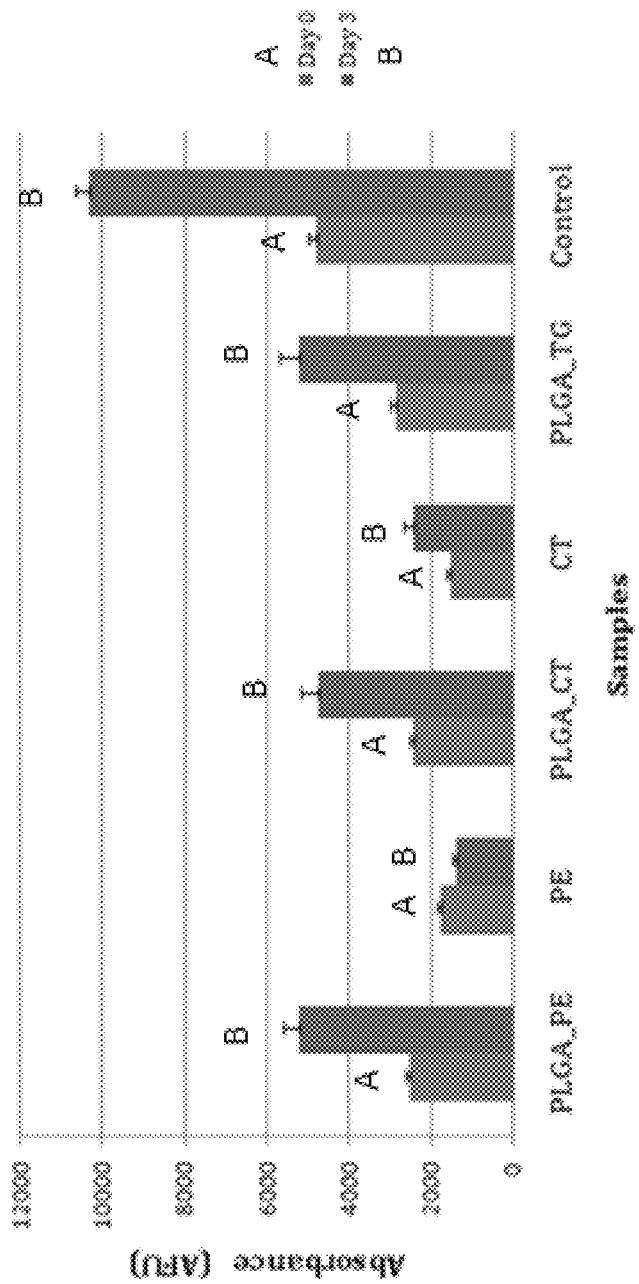
FIG. 4 is a bar graph illustrating the Alamar Test corresponding to the H9C2 initial cell adhesion and proliferation on scaffolds and templates. Values are shown as means±SEM, for n=3.

ALAMARBLUE® dye was used to determine cell proliferation. At day 0, two hours after the seeding, significant differences were noted in the initial attachment of the cells to the various substrates (FIG. 4). Once attached, however, the cells grew equally well on all scaffolds, as inferred from the similarities in population doubling times ($T_{1/2}$~36 hours) for cells growing on either PLGA scaffolds or TCP. However, the proliferation of cells seeded directly onto the textile templates was significantly inhibited, suggesting that such textiles cannot provide the necessary cues for supporting cell adhesion or proliferation. This finding argues for the use of textile-templated electrospun scaffolds, rather than the textile fabric templates themselves, as biologics.

Figure 2A:
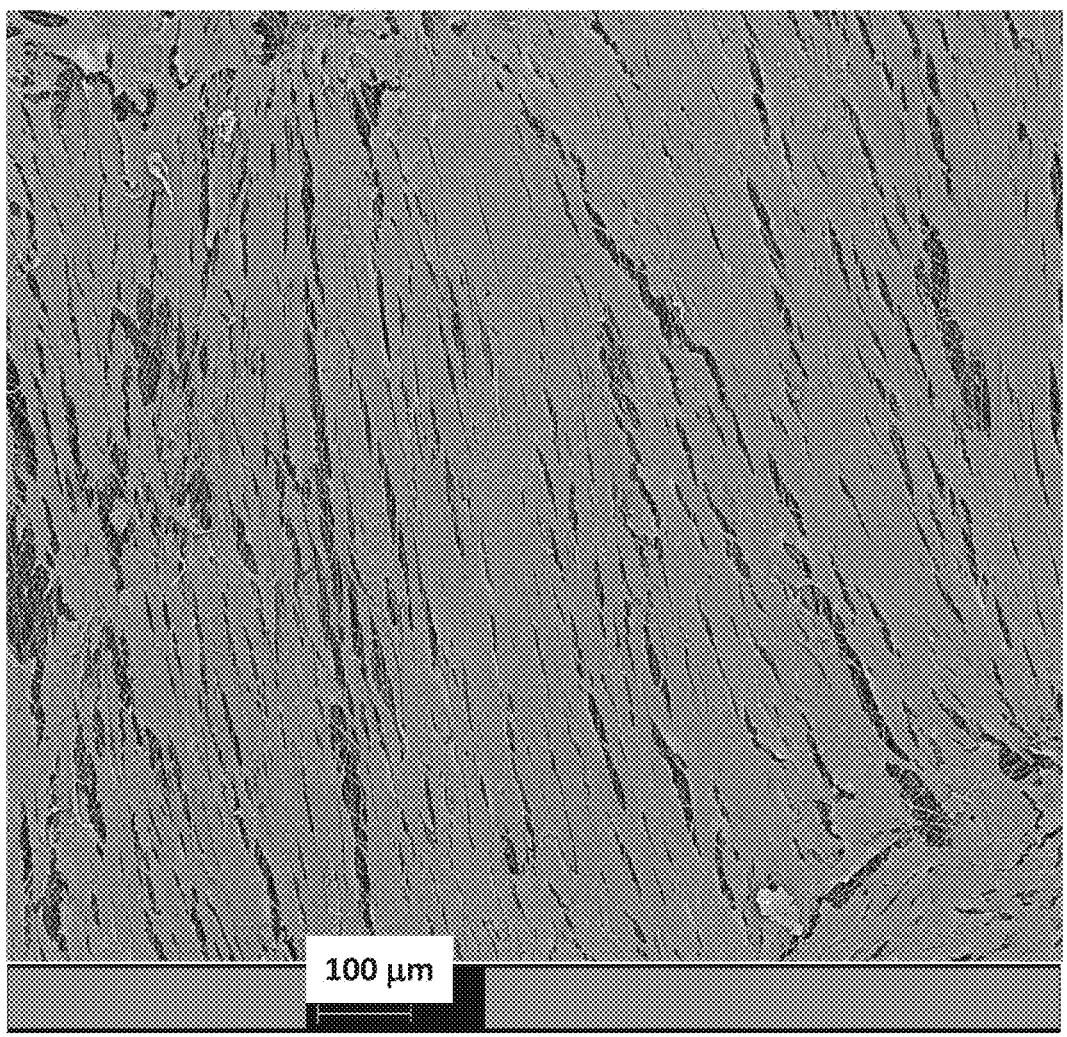
FIGS. 2A-2C, illustrates the ultrastructure of cellularized PLGA scaffolds determined by scanning electron microscopy: PLGA_PE+H9C2 (FIG. 2A), PLGA_CT+H9C2 (FIG. 2B) and PLGA_TG+H9C2 (FIG. 2C). The original magnification was 100× in all figures.
Figure 2B:
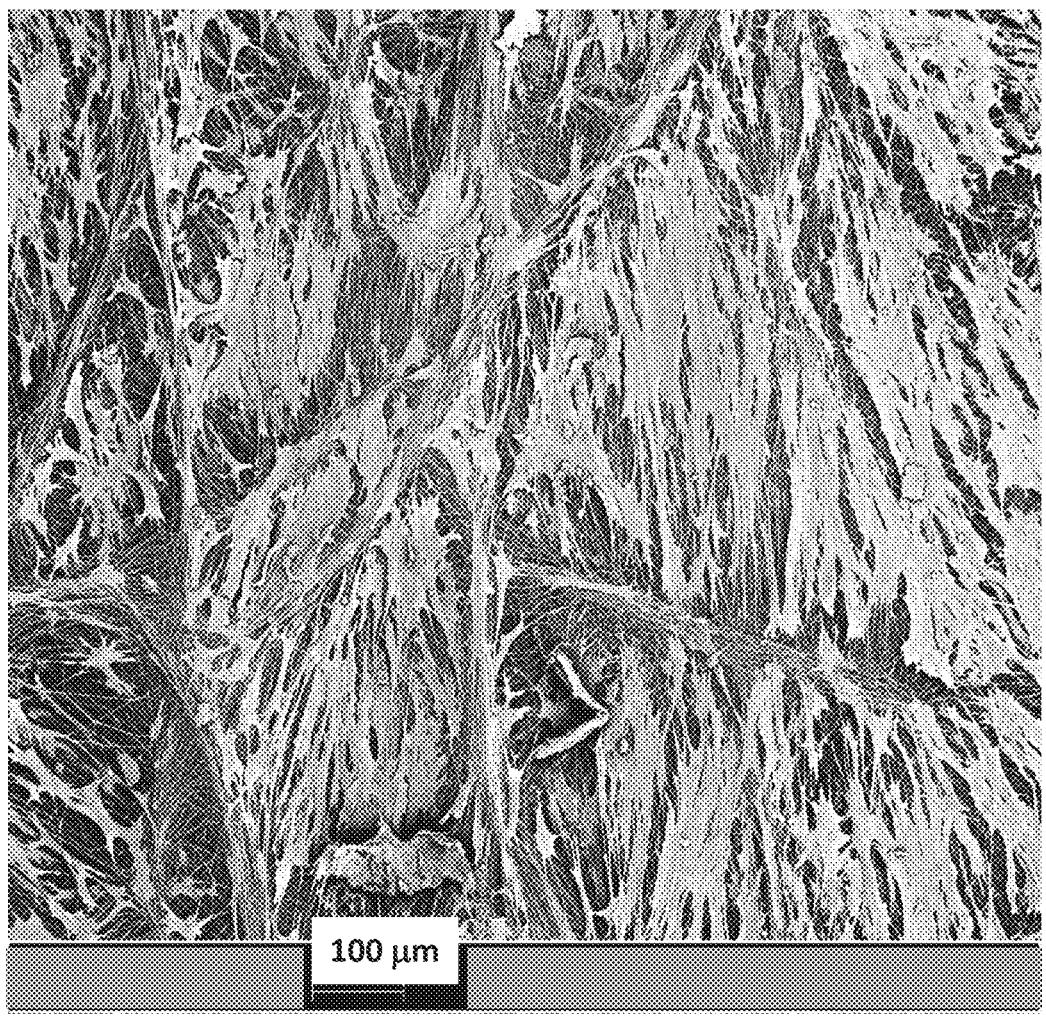
Figure 2C:
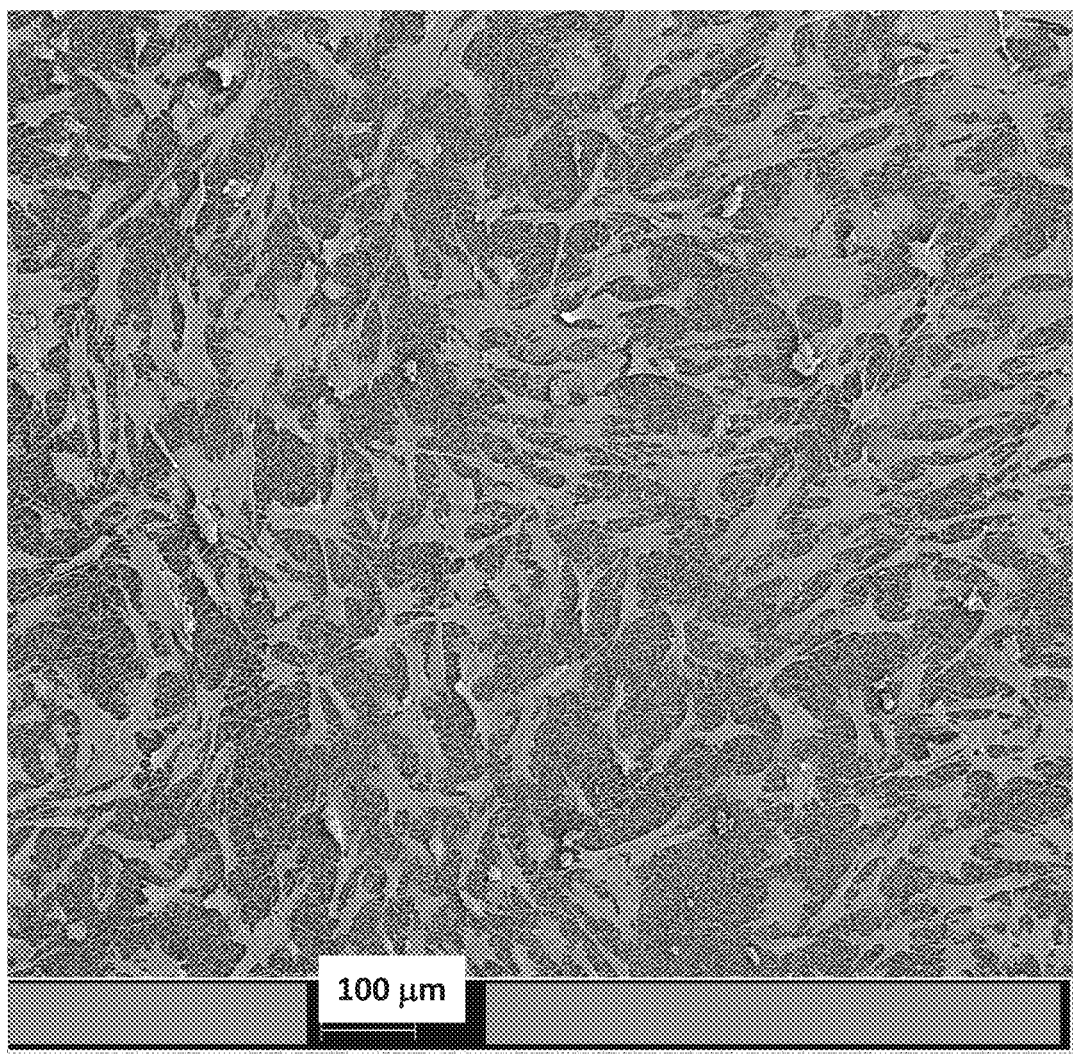
Figure 3A:
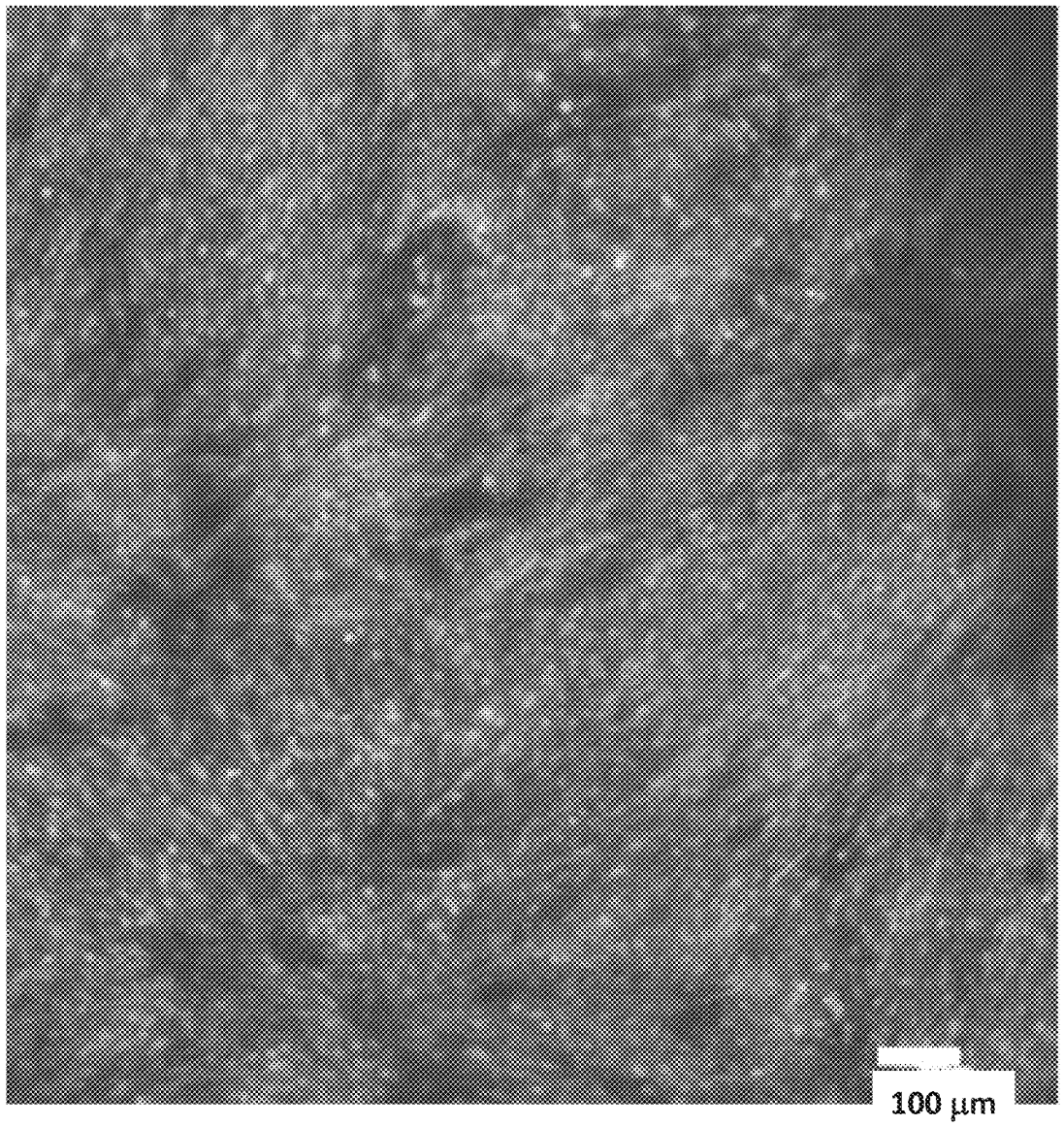
FIGS. 3A-3B, illustrates the H9C2 cell morphology on cellularized PLGA scaffolds determined by scanning electron microscopy: PLGA_PE+H9C2 (FIG. 3A) and PLGA_CT+H9C2 (FIG. 3B). The bar represents 100 µm in all figures.
Figure 3B:
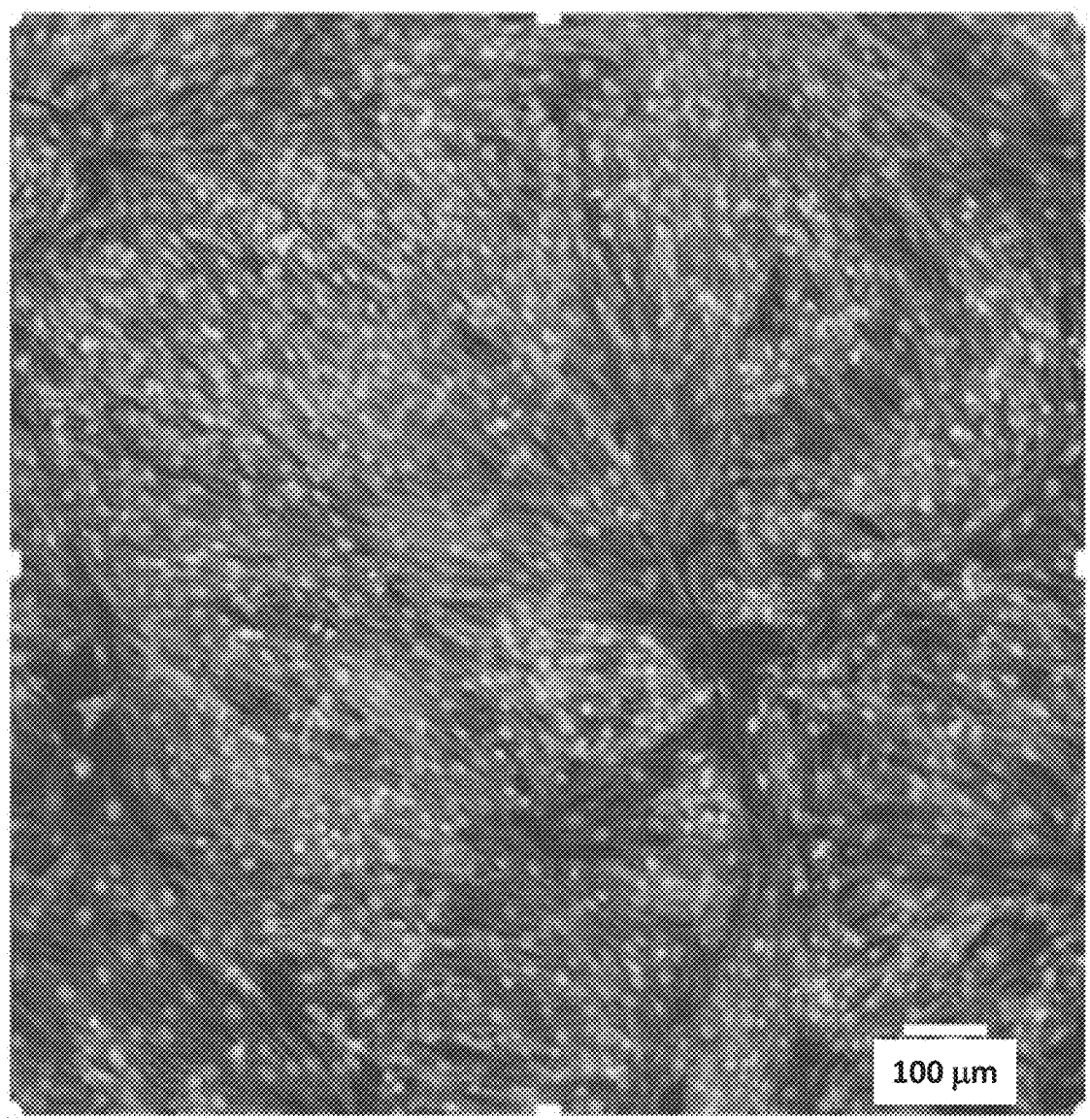

Examination of the cell alignment on the three-dimensional patterned PGLA scaffolds by SEM and confocal microscopy demonstrated that the intrinsic anisotropy of the textile-templated scaffolds is also translatable to a regional anisotropy/differential alignment of the cells growing on these scaffolds (FIGS. 2 and 3). In the literature, cellular alignment is usually observed in a vectorial dynamic environment (such as upon exposure to fluid flow or mechanical loading (Akhyari et al., 2002, Circulation 106(12) Suppl 1:1137-42) and/or upon electrical stimulation (Radisic et al., 2004, Proc. Natl. Acad. Sci. USA 101(52):18129-34). Cell alignment may also be achieved by contact guidance receiving cues from micro-patterned substrates that are usually generated through sophisticated microfabrication techniques (Engelmayr et al., 2008, Nature Materials 7(12):1003-10; Uttayarat et al., 2008, Am. J. Physiol. Heart Circ. Physiol. 294(2):H1027-35). The present experiments demonstrate a simple way to create templated scaffolds with tunable anisotropy and cell alignment based on the structural properties of inexpensive and readily-available textile fabrics.

Taken together, the results disclosed herein demonstrate a novel way to modulate the morphology and mechanical properties of electrospun scaffolds by the geometric features and physicochemical properties of textile templates. Importantly, individual patterns and aligned regions of textile-templated PLGA scaffolds provide directionality to the cells which in turn may form distinct regions of anisotropy. Textile-templated scaffolds may provide a suitable environment for the adhesion and proliferation of cardiomyoblasts and may in the future be useful as cardiac patches.

Example 3

Polycarbonate Urethanes

One of the long term goals of this investigation is to engineer an anisotropic, electrically conductive cardiac patch, which can mimic the native ECM of cardiac muscle tissue and can be used to repair damaged cardiac muscle tissue. Polycarbonate urethanes, commercially available biocompatible elastomers with mechanical properties closer to those of soft tissues, were investigated. The polycarbonate urethane used in these studies was BIONATE® (DSM PTG, Berkeley, Calif.). In order to attain electrical conductance of the cardiac muscle tissue, the polycarbonate urethane was co-electrospinned with polyaniline (PANI).

In studies with PLGA, unique patterns of scaffolds were obtained by using polyester and cotton fabrics and flat copper target as template (see Example 1). Similarly successful results were obtained by using an elastomeric polyurethane (BIONATE®, FIG. 5), demonstrating that the present approach can be applied to a variety of biomaterials. The mechanical analysis of the materials is illustrated in Table 3.

TABLE 3

Young's modulus of the Bionate ® scaffolds under 30% and 50% strain on different orientations (x and y axis)

|  | At 30% Strain | At 50% Strain |
|---|---|---|
| Bionate ®_PE (along-x axis) | 0.8283 MPa | 0.7867 MPa |
| Bionate ®_PE (along-y axis) | 0.796 MPa | 0.762 MPa |
| Bionate ®_CT (along-x axis) | 1.2595 MPa | 1.2932 MPa |
| Bionate ®_CT (along-y axis) | 1.0253 MPa | 1.0593 Mpa |
| Bionate ®_TG (along-x axis) | 1.1342 MPa | 1.0647 MPa |
| Bionate ®_TG (along-y axis) | 1.5446 MPa | 1.4637 MPa |

As illustrated in Table 3, differences in the Young's modulus of the scaffolds were observed depending on the structural pattern of each scaffold. The mechanical properties of the BIONATE® scaffolds were somewhat higher than those of mouse myocardium Young's modulus (stiffness, which is in the range of 10-500 kPa), but close to published values for other cardiac patches (Chen et al., 2008, Biomat. 29:47; Hidalgo-Bastida et al., 2007, Acta Biomat. 3:457).

Example 4

H9C2 Cell Proliferation

Figure 6:
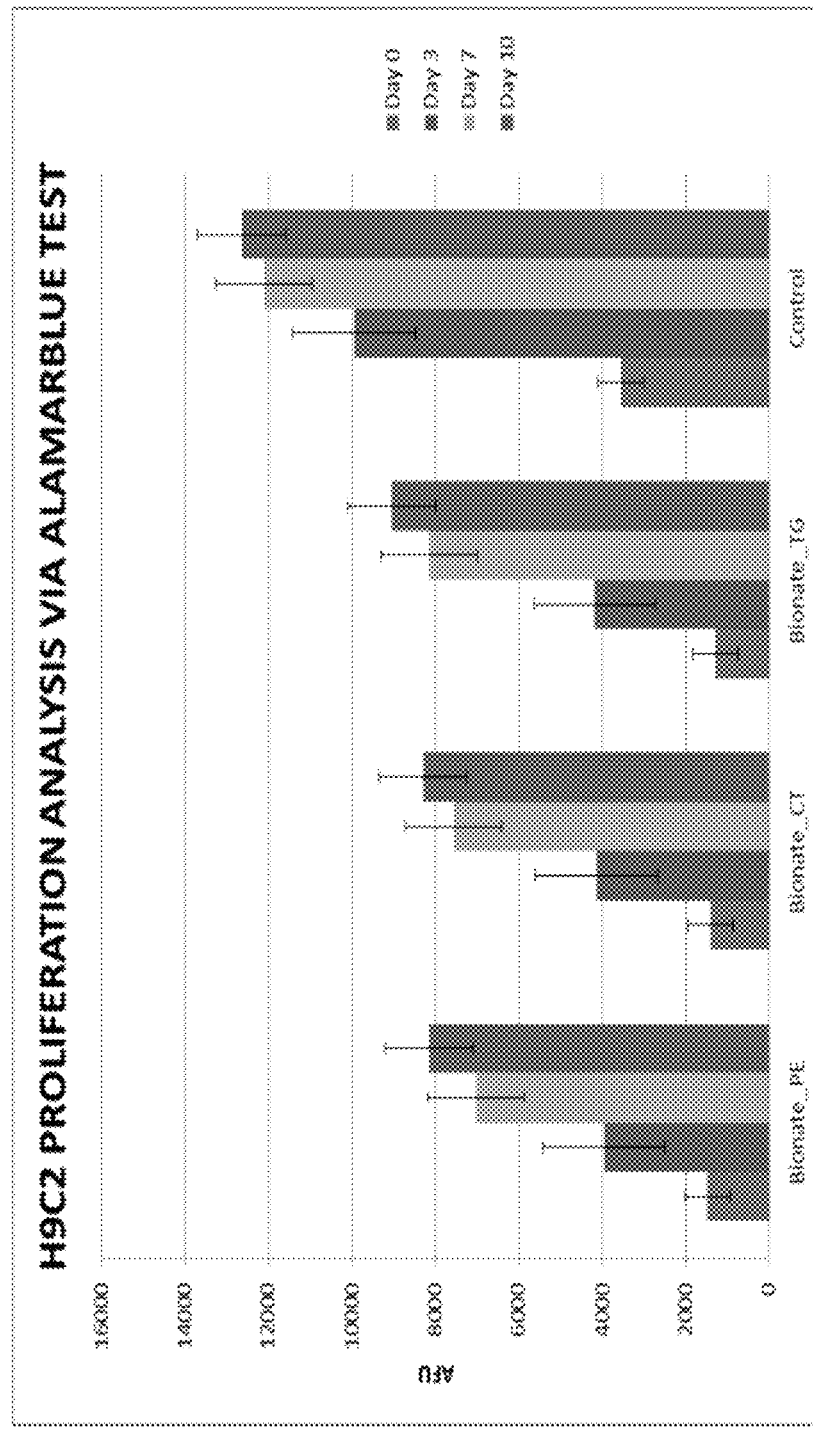
FIG. 6 is a bar graph illustrating H9C2 cell proliferation on BIONATE® scaffolds as assessed via ALAMARBLUE® test.

As illustrated in Example 2, textile template PLGA scaffolds provided a suitable environment for the attachment and proliferation of H9C2 cardiac myoblasts. Similar results were observed for the elastomeric BIONATE® scaffolds (FIG. 6). Initial cell adhesion on BIONATE® scaffolds was found to be lower than the PLGA scaffolds, however the rate of cell proliferation was significantly higher on the BIONATE® scaffolds than the PLGA scaffolds (FIGS. 6 and 4).

Example 5

Conductive Property

PANI polymer was blended with a polycarbonate urethane (BIONATE®) in various concentrations, and their conductive properties were evaluated (Table 4). PANI has been used in literature to bring in conductive property to the scaffolds for cardiac and nerve tissue engineering (Li et al., 2006, Biomat. 27:2705; Ghasemi-Mobarakeh et al., 2009, Tissue Eng.: Part A 3605).

TABLE 4

Concentration of PANI and Bionate ® in mixed solution

| | Mass in 5 mL | | Final percentage (%) | |
|---|---|---|---|---|
| ratios | Bionate ® | PANI | Bionate ® | PANI |
| Bionate ® (control) | 400 mg | 0 | 8 | 0 |
| 90:10 | 450 mg | 1.5 mg | 9 | 0.03 |
| 85:15 | 425 mg | 2.25 mg | 8.5 | 0.045 |
| 80:20 | 400 mg | 3 mg | 8 | 0.06 |
| 70:30 | 350 mg | 4.5 mg | 7 | 0.09 |
| 60:40 | 300 mg | 6 mg | 6 | 0.12 |

Figure 7:
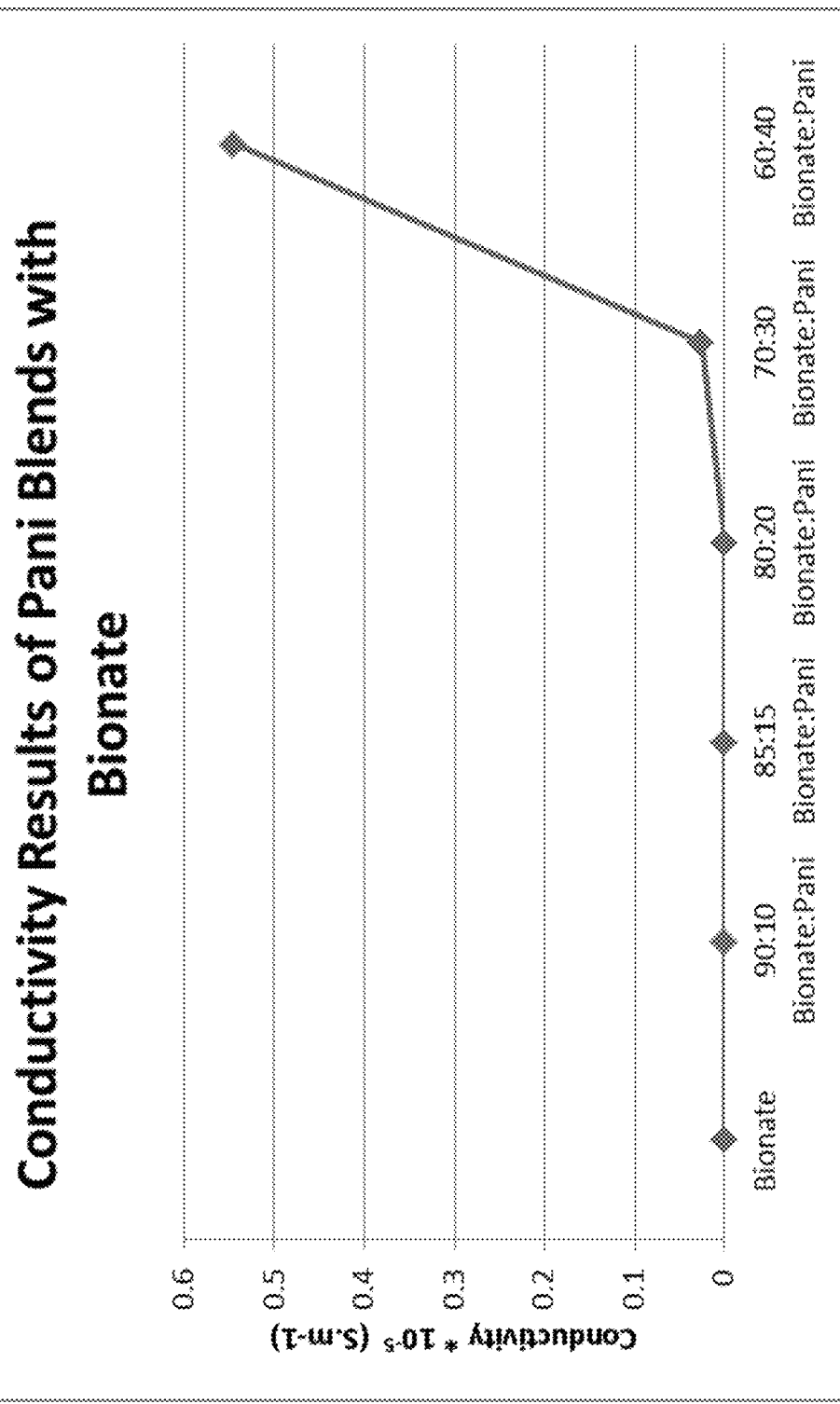
FIG. 7 is a graph illustrating the conductivity of BIONATE®-PANI blended scaffolds.

As illustrated in FIG. 7, the conductivity analysis showed an increase in conductivity in the 70:30 and 60:40 mixes. The conductivities of these scaffolds are in the range of conductivities observed stated in nerve tissue engineering (Ghasemi-Mobarakeh et al., 2009, Tissue Eng.: Part A 3605).

The methods disclosed herein are applicable for different kinds of polymer with various mechanical properties. The tissue scaffolds exhibit structural and mechanical anisotropy. Therefore, it is possible to use these methods to engineer biomimetic scaffolds for various tissue types.

The conductive polymers useful within these methods include, but are not limited to, PANI, polypyyrole and PEDOT (poly(3,4-ethylenedioxythiophene). The conductivity of BIONATE®-conductive polymers scaffolds may be identified and improved, and the effects of electrical stimulation on cardiac myoblast differentiation and cardiac myocyte function ("beating" tissue) may be assessed.

The cellular analyses may be carried out in a "static" environment, or in dynamic environments (first in vitro, using a Flexcell system). Ultimately, a "beating" cardiac patch may be generated and tested in vivo upon implantation in rat MI model.

Example 6

Textile-Templated Co-Electrospun Blends of PLGA, Gelatin, and Elastin for Myocardial Tissue Engineering Research Progress Poly(glycerol-sebacate) (PGS) is viewed a promising biomaterial for myocardial tissue engineering, with mechanical properties consistent with those of the human myocardium (Qi-Zhi Chen et al., 2008, Mat. Sci. Eng. Rev. 59:1-37), but may not be suitable for electrospinning.

Blends of PLGA, gelatin, and elastin ("PGE") were investigated because the PGE mats are elastic and the corresponding Young's modulus is close to that of human myocardium (Han et al., 2011, Biomacromol. 12:399-408). Furthermore, PGE has excellent biocompability with H9C2 myoblasts (Li et al., 2006, J. Biomed. Mater. Res. A 79(4): 963-73).

Anisotropic textile templates were used as a simpler and cheaper method to fabricate anisotropic nanofiber scaffolds. Blends of PLGA, gelatin and elastin (PGE) were co-electrospun on Jersey knit templates. Jersey knit structure, the simplest weft knit structure, is porous and mechanically anisotropic and elastic. In addition, hybrid constructs made from heart cells, fibrin, and biodegradable elastomeric knit fabric were successfully applied to cardiac tissue engineering by the other group (Boublik et al., 2005, Tissue Eng. 11(7/8):1122-32).

The fibrous morphology and alignment/anisotrophy of the elastomeric and anisotropic PGE fibrous scaffolds prepared by co-electrospinning blends of PLGA, gelatin and elastin on Jersey knit templates were investigated by scanning electron microscope (SEM). The elastic and anisotropic mechanical properties of the scaffolds were studied by Instron 5500. Atomic force microscopy (AFM) may be used to detect the scaffold surface topography. In order to evaluate the bioactivity of patterned PGE fibrous scaffolds, BBZ/Phalloidin immunostaining and ALMARBLUE® dye may be used to investigate cell morphology and alignment and cell proliferation on the scaffolds, respectively.

Figure 8:
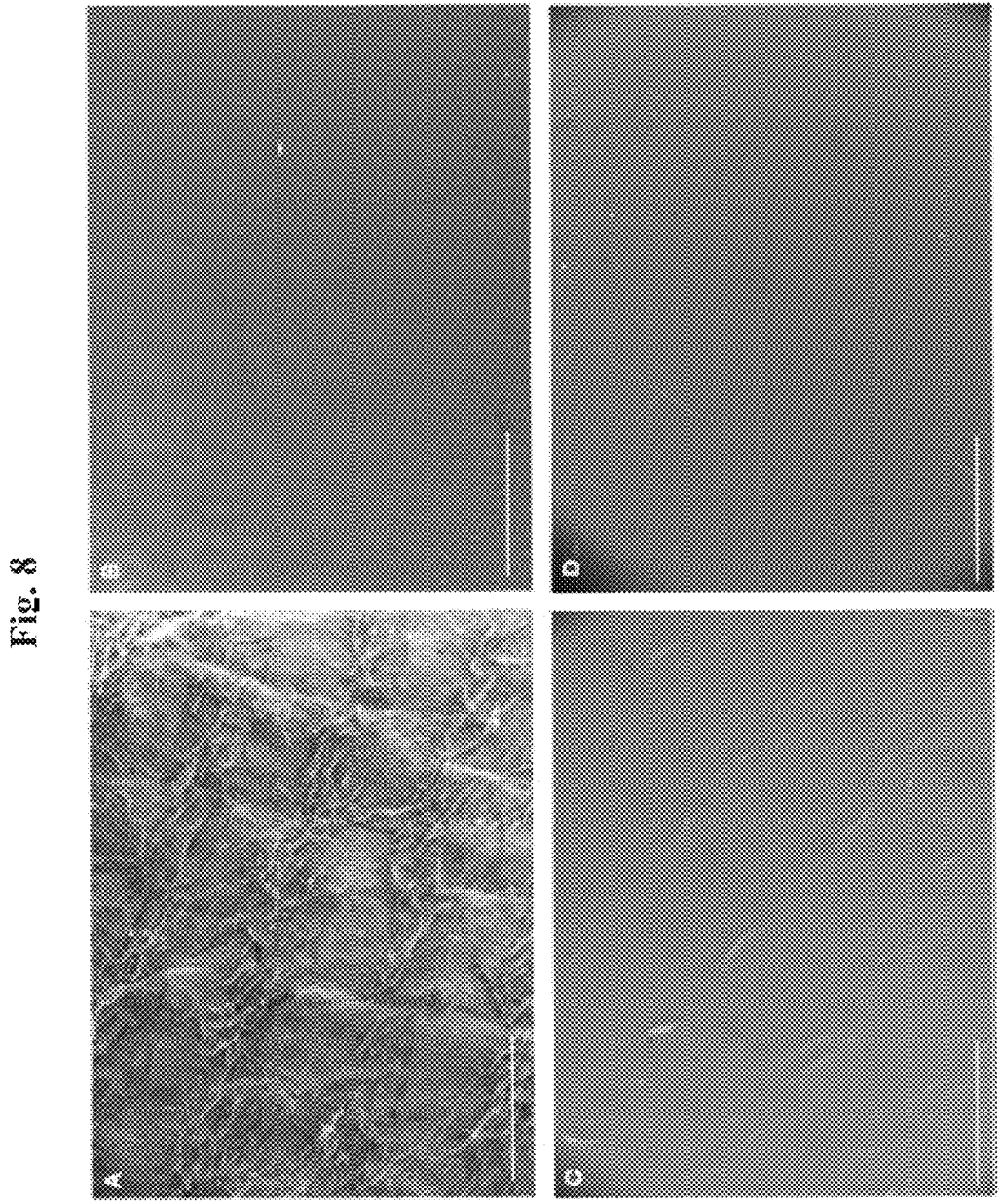
FIG. 8, comprising Panels 8A-8D, corresponds to SEM images of PGE 241 nanofibrous scaffolds (scale bars: 1 mm). PLGA, gelatin, and elastin were dissolved in 1,1,1,3,3,3-hexafluoro-2-propanol (HFP) at 10, 8, and 20%, respectively, then mixed as blends at volume ratios of 2:4:1. Panel 8A: dry PGE 241 patterned scaffold. Panel 8B: dry PGE 241 plain scaffold. Panel 8C: hydrated PGE 241 patterned scaffold. Panel 8D: hydrated PGE 241 plain scaffold.
Figure 10A:
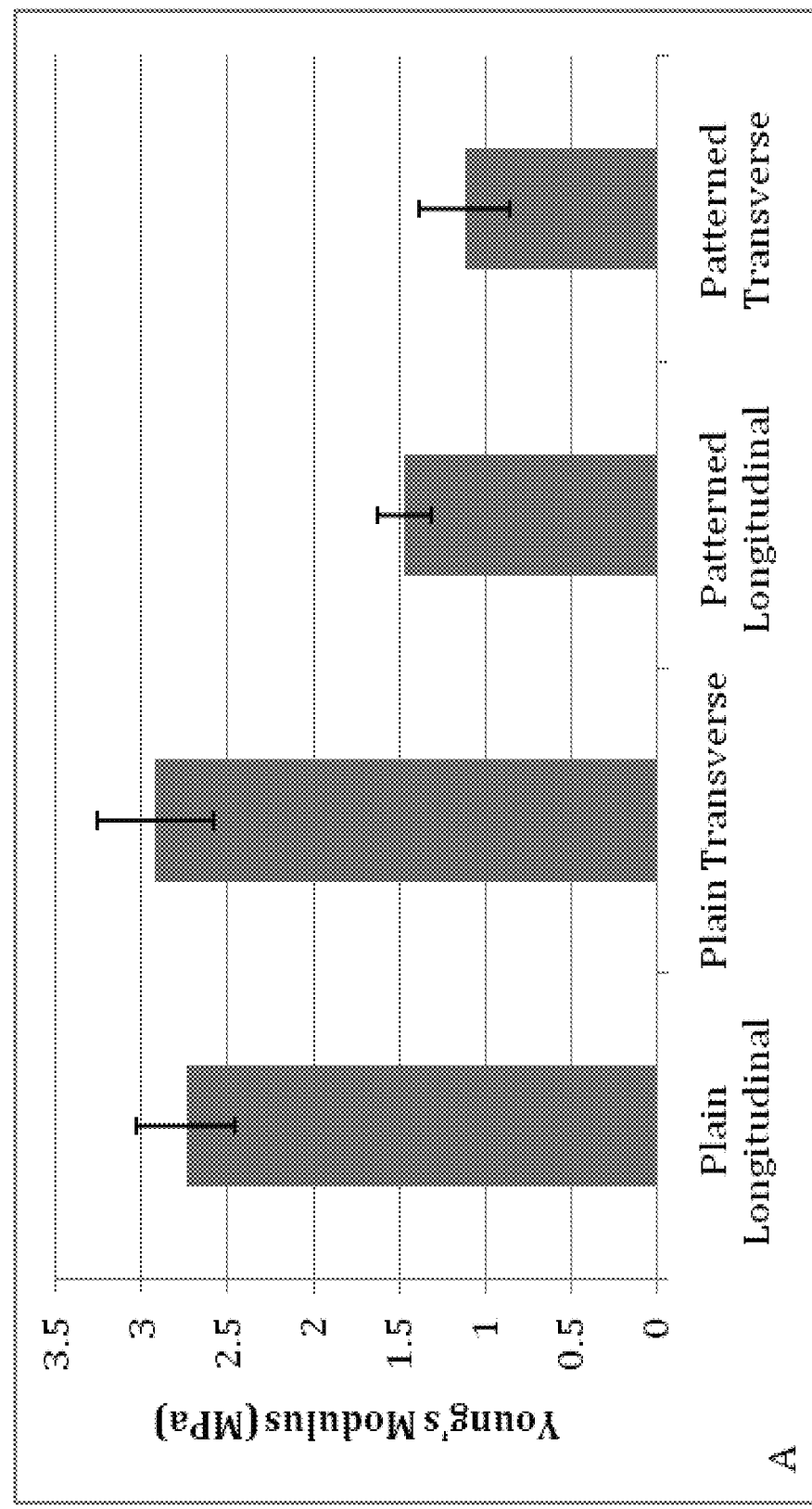
FIGS. 10A-10B, is a set of bar graphs that illustrate Young's modulus (FIG. 10A) and tensile strength (FIG. 10B) of hydrated PGE 241 nanofibrous scaffolds (P value between plain longitudinal and transverse scaffolds>0.05, while P value between patterned longitudinal and transverse scaffolds<0.05).
Figure 10B:
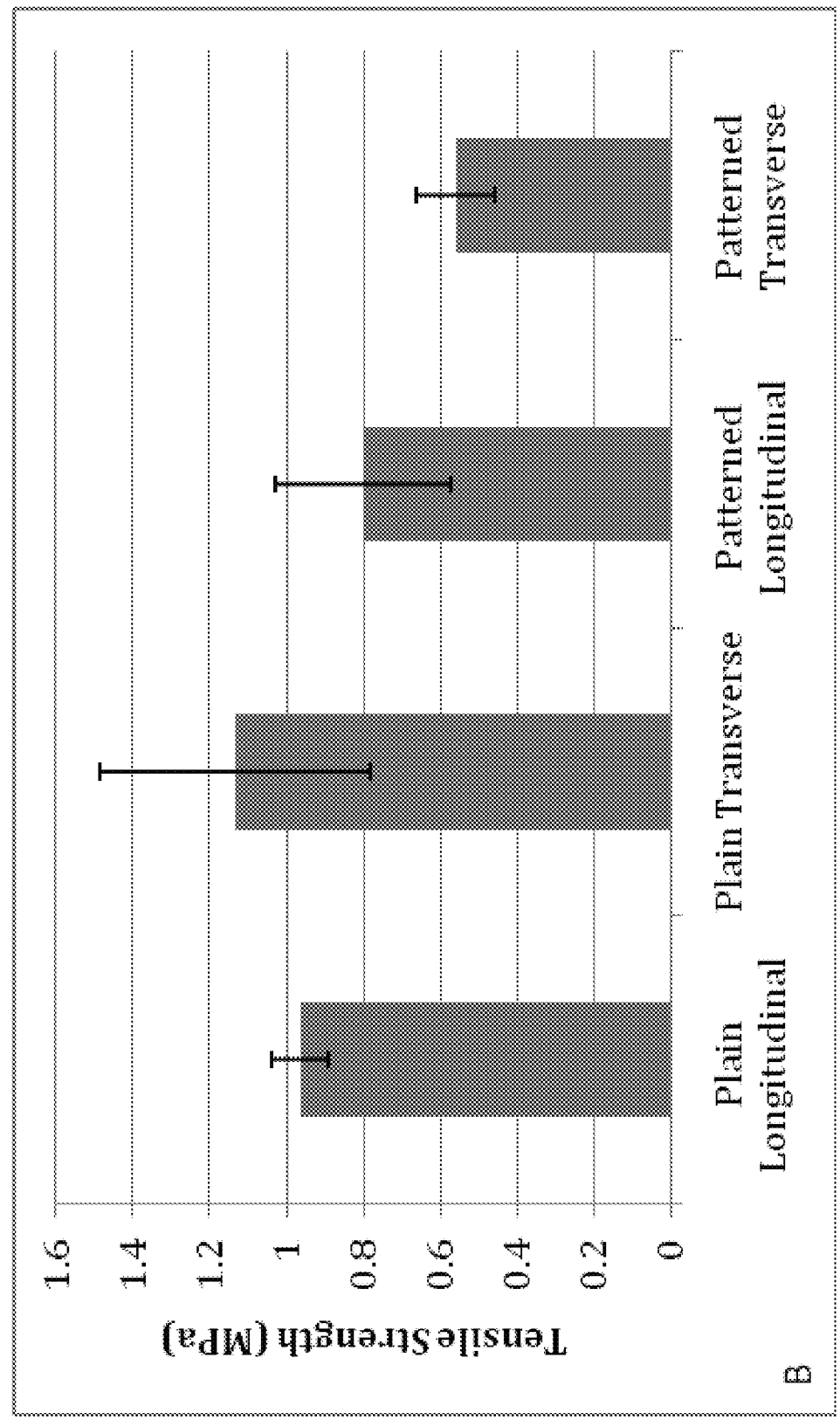

Using SEM and Instron 5500 (FIG. 8), the clear ridged alignment on the patterned nanofibrous scaffolds was observed, as compared with the plain nanofibrous scaffolds in both dry and hydrated conditions. There was no appreciable difference in fiber diameter between the dry plain and dry patterned nanofibrous scaffolds, while the hydrated patterned scaffolds presented finer fibers than hydrated plain scaffolds (FIG. 9). Furthermore, mechanically anisotropic PGE patterned scaffolds were obtained. The Young's modulus of the hydrated patterned PGE scaffolds was 2 times lower than that of the plain scaffolds, indicating higher elasticity. The Young's modulus of the hydrated patterned PGE scaffolds was relatively closer to that of the human myocardium as 0.5 MPa.

The H9C2 myoblasts interaction with PGE nanofibrous scaffolds (cell morphology, proliferation) for the potential anisotropic effects of templated PGE nanofibrous scaffolds may be investigated. Moreover, the scaffold surface topography in both dry and hydrated conditions may be evaluated by using AFM.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A method of preparing an anisotropic scaffold, comprising the steps of:
   electrospinning a solution of matrix material in a solvent upon an anisotropic textile template to form said anisotropic scaffold; and
   peeling said anisotropic scaffold from said anisotropic textile template.

2. The method of claim 1, wherein said matrix material comprises a protein or a polymer.

3. The method of claim 2, wherein said polymer is selected from the group consisting of poly(urethane), poly(siloxane), poly(ethylene), poly(vinyl pyrrolidone), poly(2-hydroxy ethyl methacrylate), poly(N-vinyl pyrrolidone), poly(methyl methacrylate), poly(vinyl alcohol), poly(acrylic acid), polyacrylamide, poly(ethylene-co-vinyl acetate), poly(ethylene glycol), poly(methacrylic acid), polylactide, polyglycolide, poly(lactide-co-glycolide), polyanhydride, polyorthoester, polycarbonate, and combinations and co-polymers thereof.

4. The method of claim 2, wherein said polymer is co-span with at least one compound selected from the group consisting of gelatin, elastin and mixtures thereof.

5. The method of claim 2, wherein said polymer is co-span with at least one conductive polymer.

6. The method of claim 5, wherein said conductive polymer is selected from the group consisting of polyfluorene, polyphenylene, polypyrene, polyazulene, polynaphthalene, polypyrrole, polycarbazole, polyindole, polyazepine, polyaniline, polythiophene, poly(3,4-ethylenedioxythiophene), poly(p-phenylene sulfide), polyacetylene, poly(p-phenylene vinylene), and combinations and co-polymers thereof.

7. The method of claim 1, wherein said matrix material is biocompatible and cytocompatible.

8. The method of claim 1, wherein said solvent is selected from the group consisting of water, urea, methylene chloride, cyclohexane, diethyl ether, 1,4-dioxane, furan, tetrahydrofuran, ethanol, isopropanol, propane-1,3-diol, ethylene glycol, diethylene glycol, glycerine, acetone, 2-butanone, ethyl acetate, methyl formate, acetonitrile, acetamide, dimethylacetamide, N-methylformamide, N,N-dimethylformamide, N-methyl pyrrolidone, N-methyl morpholine-N-oxide, dimethylsulfoxide, formic acid, acetic acid, hydrochloric acid, maleic acid, 1,1,1-trifluoroacetone, hexafluoroacetone, 2,2,2-trifluoroethanol, 1,1,1,3,3,3-hexafluoro-2-propanol, monochloroacetic acid, trifluoroacetic acid, trifluoroacetic anhydride, triethanolamine, indole, piperazine, pyrrole, 2-pyrrolidone, pyridine, quinoline, tetrahydroquinoline, pyrazole, imidazole, and combinations thereof.

9. The method of claim 1, wherein said anisotropic textile template is an elastic fabric.

10. The method of claim 1, wherein said anisotropic textile template is an polyester fabric.

11. The method of claim 1, wherein said anisotropic textile template is an cotton fabric.

12. The method of claim 1, wherein said anisotropic textile template is a woven fabric.

13. The method of claim 1, wherein said anisotropic textile template is a knitted fabric.

14. The method of claim 13, wherein said knitted fabric is a Jersey-knitted fabric.

15. The method of claim 13, wherein said knitted fabric has between about 6 wale/cm to about 10 wale/cm.

16. The method of claim 13, wherein said knitted fabric has 7 wale/cm.

17. The method of claim 13, wherein said knitted fabric has 8.5 wale/cm.

18. The method of claim 13, wherein said knitted fabric has between about 6 course/cm to about 8 course/cm.

19. The method of claim 13, wherein said knitted fabric has about 16 course/cm.

20. The method of claim 13, wherein said knitted fabric has a yarn number between about 15 tex to about 75 tex.

21. The method of claim 13, wherein said knitted fabric has a yarn number between about 20 tex to about 60 tex.

22. The method of claim 13, wherein the knitted fabric:
   is a Jersey-knitted polyester fabric;
   has between about 6 wale/cm to about 10 wale/cm;
   has between about 6 course/cm to about 8 course/cm; and
   a yarn number between about 15 tex to about 75 tex.

23. The method of claim 13, wherein the knitted fabric:
   is a Jersey-knitted polyester fabric;
   has 8.5 wale/cm;
   has between 16 course/cm; and
   a yarn number of 21.24 tex.

24. The method of claim 23, wherein the knitted fabric: has a weight of 142.39 g/m².

25. The method of claim 23, wherein the knitted fabric: has a thickness of 1.029 mm.

* * * * *